(12) United States Patent
Ida et al.

(10) Patent No.: US 8,111,807 B2
(45) Date of Patent: Feb. 7, 2012

(54) CRYSTALLITE SIZE ANALYSIS METHOD AND APPARATUS USING POWDER X-RAY DIFFRACTION

(75) Inventors: Takashi Ida, Nagoya (JP); Licai Jiang, Rochester Hills, MI (US)

(73) Assignee: Rigaku Corporation, Akishima-Shi, Tokyo (JP)

(*) Notice: Subject to any disclaimer, the term of this patent is extended or adjusted under 35 U.S.C. 154(b) by 97 days.

(21) Appl. No.: 12/560,803

(22) Filed: Sep. 16, 2009

(65) Prior Publication Data

US 2011/0064199 A1 Mar. 17, 2011

(51) Int. Cl.
*G01N 23/207* (2006.01)
*G01N 23/20* (2006.01)

(52) U.S. Cl. .......... 378/75; 378/70; 378/71; 378/73

(58) Field of Classification Search .......... 378/70–75, 378/79, 80, 201
See application file for complete search history.

(56) References Cited

U.S. PATENT DOCUMENTS

| | | | | |
|---|---|---|---|---|
| 3,609,356 | A * | 9/1971 | Schwuttke et al. | 378/74 |
| 5,748,509 | A * | 5/1998 | Fewster | 703/6 |
| 6,385,289 | B1 * | 5/2002 | Kikuchi | 378/79 |
| 6,751,287 | B1 * | 6/2004 | Kalyon et al. | 378/71 |
| 7,123,686 | B2 * | 10/2006 | Sakata | 378/71 |
| 7,206,378 | B2 * | 4/2007 | Obata et al. | 378/71 |
| 7,583,789 | B1 * | 9/2009 | MacDonald et al. | 378/84 |
| 2008/0159479 | A1 * | 7/2008 | Huang et al. | 378/73 |

OTHER PUBLICATIONS

T. Ida et al., "Diffraction Peak Profiles from Spherical Crystallites with Lognormal Size Distribution", Journal of Applied Crystallography, Oct. 2003, pp1107-1115, vol. 36, Part 5, ISSN 0021-8898.
T. Ida, "Statistical Properties of Powder Diffraction Data", The ICDD 2009 Spring Meetings Reports of Technical Regional Co-Chairs, Mar. 26, 2009, ICDD Headquarters, Newtown Square PA, USA.
T. Ida et al., "Evaluation of Particle Statistics in Powder Diffractometry by a Spinner-Scan Method", Journal of Applied Crystallography, Aug. 2009, pp. 597-606, vol. 42, Part 4, ISSN 0021-8898.
M. Teich, "Normalizing Transformations for Dead-Time-Modified Poisson Counting Distributions," Biological Cybernetics, 1985, No. 53, pp. 121-124.

(Continued)

*Primary Examiner* — Anastasia Midkiff
(74) *Attorney, Agent, or Firm* — Buchanan Ingersoll & Rooney PC

(57) ABSTRACT

A sample is supported on a flat rotary specimen stage and irradiated at an incidence angle θ via a divergence slit with an x-ray beam emitted by an x-ray source, the diffraction beam from the sample is received via a divergence slit and the light-receiving slit by an x-ray detector placed at the position of a diffraction angle 2θ to generate diffraction beam intensity data, the x-ray incidence angle θ and diffraction angle 2θ are fixed at intrinsic values on the sample, the sample is rotated within a plane at designated step angles by the flat rotary specimen stage, the diffraction beam intensity is measured by the x-ray detector in each in-plane rotation step, the variance induced by particle statistics is calculated from the calculated diffraction beam intensities, and the size of the crystallites in the sample is calculated based on the variance induced by the particle statistics.

4 Claims, 14 Drawing Sheets

OTHER PUBLICATIONS

L. Alexander et al., "Statistical Factors Affecting the Intensity of X-Rays Diffracted by Crystalline Powders," Journal of Applied Physics, 1948, No. 19, pp. 742-753.

P. De Wolff, "Particle Statistics in X-Ray Diffractometry," Appl. Sci. Res, 1958, Section B. vol. 7, pp. 102-112.

D. Smith, "Particle Statistics and Whole-Pattern Methods in Quantitative X-Ray Powder Diffraction Analysis," Dec. 2001, Powder Diffraction, vol. 16, No. 4, pp. 186-191.

S. Freiman et al., "Certificate: Standard Reference Material® 640c," National Institute of Standards & Technology, Sep. 13, 2000, Gaithersburg, MD USA.

F. Izumi et al., "A Rietveld-Analysis Program RIETAN-98 and Its Application to Zeolites," Material Science Forum, 2000, vols. 321-324, pp. 198-203.

T. Ida et al., "Deconvolution of the Instrumental Functions in Powder X-Ray Diffractometry," Applied Crystallography, 2002, No. 35, pp. 58-68.

\* cited by examiner

SEM IMAGE OF STANDARD Si POWDER
(NIST SRM640c)

EXTRACTED PARTICLE
PROFILES FROM FIG. 1A

SEM IMAGE OF 3-7 μm FRACTION
OF α-QUARTZ POWDER

SEM IMAGE OF 8-12 μm FRACTION
OF α-QUARTZ POWDER

SEM IMAGE OF 18-22 μm FRACTION OF α-QUARTZ POWDER

⊙ : PRODUCT OF THE EFFECTIVE
   NUMBER OF CRYSTALLITES BY $\sin\theta$ $m_{eff}$ : KNOWN EFFECTIVE MULTIPLICITY
        OF REFLECTION FOR Si ⊙ : EFFECTIVE DIAMETER $D'_{eff}$
OF Si POWDER CALCULATED BY
ASSUMED INSTRUMENTAL PARAMETERS ⊙ : CALIBRATED EFFECTIVE DIAMETER
$D_{eff}$ OF Si POWDER

FIG. 9A

EFFECTIVE MULTIPLICITY OF REFLECTION $M_{eff}$ FOR Si PREDICTED BY THE KNOWN CRYSTAL STRUCTURE

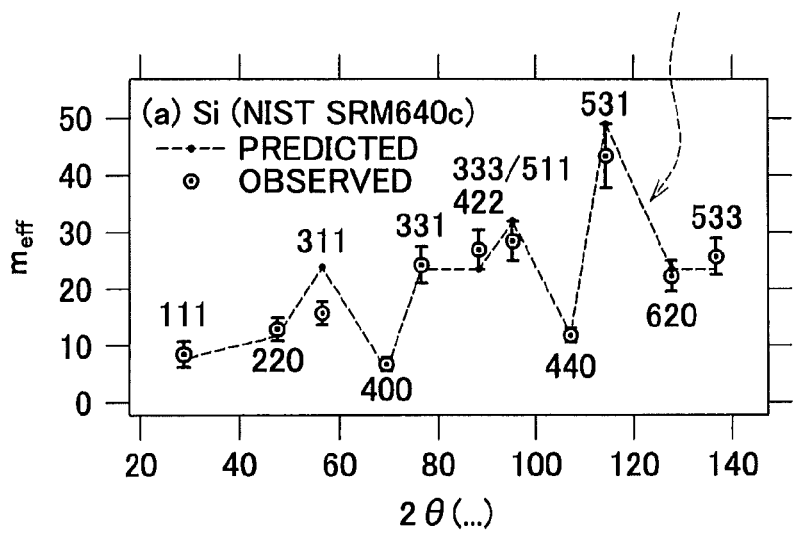

⊙ : EFFECTIVE MULTIPLICITY OF REFLECTION $M_{eff}$ FOR Si EVALUATED BY THE SPINNER-SCAN MEASUREMENT

FIG. 9B

EFFECTIVE MULTIPLICITY OF REFLECTION $M_{eff}$ FOR 8-12 $\mu$m QUARTZ SAMPLE PREDICTED BY THE KNOWN CRYSTAL STRUCTURE

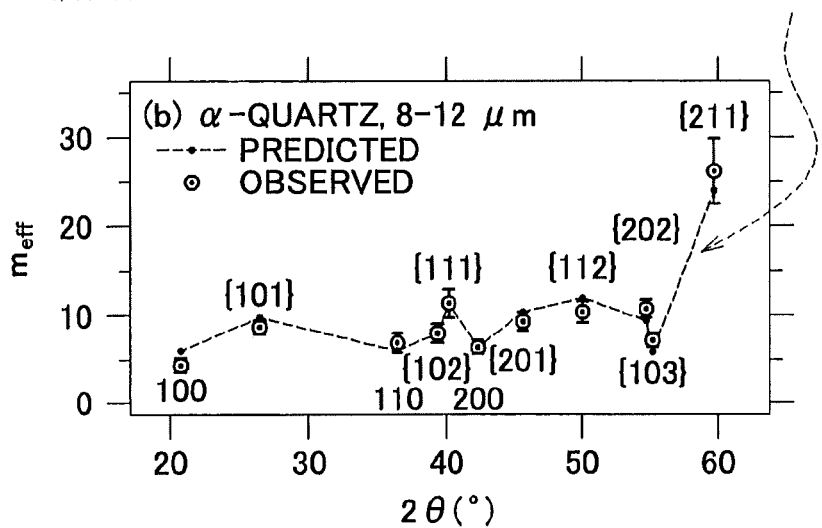

⊙ : EFFECTIVE MULTIPLICITY OF REFLECTION $M_{eff}$ FOR 8-12 $\mu$m QUARTZ SAMPLE EVALUATED BY THE SPINNER-SCAN MEASUREMENT

US 8,111,807 B2

CRYSTALLITE SIZE ANALYSIS METHOD AND APPARATUS USING POWDER X-RAY DIFFRACTION

BACKGROUND OF THE INVENTION

1. Field of the Invention

The present invention relates to a crystallite size analysis method and a crystallite size analysis apparatus for sampling intensity data of a diffraction beam exiting or being generated from a powder sample when the sample is irradiated with an x-ray beam, and determining, based on the diffraction beam intensity data, the size of crystallites included in the powder sample.

2. Description of the Related Art

The crystallite size of crystals contained in a substance is an important factor that has an effect on the characteristics of the substance. For example, the crystallite size sometimes has an effect on drug characteristics such as degradability, fluidity, and stability. Analytical methods based on x-ray diffraction line-broadening analysis are conventionally known as methods for analyzing the size of crystallites.

When a sample prepared from a substance that is a diffraction target is irradiated with an x-ray beam, a diffraction beam is commonly generated from the sample if designated diffraction conditions, such as the Bragg diffraction conditions, are satisfied between the x-ray beam and the sample.

As is schematically shown in FIG. 11, when a diffraction beam R2 is generated from a sample S, the diffraction beam R2 escapes from the sample S at an angle $2\theta$ that is twice the incidence angle $\theta$ of the incident x-ray beam R1 relative to an extension line drawn to the opposite side of the sample, where $\theta$ is the incidence angle of the x-ray beam R1 that strikes the sample S in relation to the sample S. The angle $2\theta$ of the diffraction beam R2 to the corresponding incident x-ray beam R1 is referred to as the diffraction angle $2\theta$.

In a common x-ray diffraction measurement, the x-ray incidence angle $\theta$ is continuously or intermittently varied at a designated angular velocity, and the angle at which the sample is perceived by an x-ray detector is varied at the same angular velocity as the incidence angle $\theta$. In the process, the diffraction beam emitted by the sample S at a diffraction angle $2\theta$ is detected by the x-ray detector. The intensity of the diffraction beam detected by the x-ray detector in this manner is plotted as a diffraction beam diagram or diffraction beam profile P on a system of coordinates having the diffraction angle $2\theta$ and diffraction beam intensity I as orthogonal axes, as shown in FIG. 12, for example.

It is known that the width W (see FIG. 13) of each diffraction peak in the diffraction beam profile P does not remain constant all the time but varies in accordance with the size of the crystallites that form the sample S. Specifically, it is believed that the peak width W of a diffraction beam increases with smaller crystallites, and decreases with larger crystallites.

The method for analyzing the crystallite size based on the aforementioned x-ray diffraction line-broadening analysis is an analysis method for evaluating the crystallite size on the basis of the size of the diffraction beam peak width in such a diffraction beam profile. More specifically, the crystallite size D can be calculated using $$D = K\lambda / \beta \cos \theta,$$

where $\lambda$ is the wavelength of the x-ray beam, $\beta$ is the width of the diffraction beam, $\theta$ is the Bragg angle of the diffraction beam, and K is the Scherrer constant. Here, K is a constant determined depending on the definition of the crystallite size and the width of the diffraction beam. Crystallites that are less than several micrometers in size can be evaluated when the size of the crystallites is evaluated using this conventional analysis technique, but it has so far been impossible to evaluate crystallites that are several micrometers or greater in size.

SUMMARY OF INVENTION

An object of the present invention, which was perfected in order to overcome the above-described problems of the prior art, is to provide a crystallite size analysis method and apparatus capable of determining the size of crystallites measuring several micrometers or greater.

(Structure of the Invention)

The crystallite size analysis method according to a first aspect is a method for sampling intensity data of a diffraction beam exiting a powder sample when the sample is irradiated with an x-ray beam, and determining, based on the diffraction beam intensity data, the size of crystallites included in the sample, the method comprising the steps of (1) supporting the sample on a flat-plate specimen spinner, (2) restricting, by using a divergence slit, the width of an x-ray beam emitted by an x-ray source, and irradiating the sample at an incidence angle $\theta$, (3) allowing the diffraction beam exiting the sample to pass through a scattering slit and a light-receiving slit while restricting the beam width by the slits, (4) receiving the diffraction beam that has passed through the light-receiving slit by an x-ray detector placed at the position of a diffraction angle $2\theta$, and generating diffraction beam intensity data $\{Ij\}$ (j=0, 1, ..., n−1) by the x-ray detector, (5) fixing the x-ray incidence angle $\theta$ and diffraction angle $2\theta$ at corresponding intrinsic values on the sample, (6) rotating the sample within a plane at a designated step angle by the flat-plate specimen spinner, (7) measuring the diffraction beam intensity $\{Ij\}$ by the x-ray detector at the position of each step along the rotation within a plane, (8) calculating the variance $\{(\Delta I_{particle})^2\}$ brought about by particle statistics from the calculated plurality of diffraction beam intensities $\{Ij\}$, and (9) calculating, based on the variance $\{(\Delta I_{particle})^2\}$ brought about by the particle statistics, the size of the crystallites included in the sample.

In the crystallite size analysis method according to a second aspect, it is possible to (1) calculate periodic drift $(I_{drift})$ from the measured plurality of diffraction beam intensities $\{Ij\}$, (2) calculate the statistical variance $(\Delta I_{obs})^2$ of deviation ($\delta I$) obtained by subtracting the periodic drift $(I_{drift})$ from the measured plurality of diffraction beam intensities $\{Ij\}$, and (3) calculating the variance $\{(\Delta I_{particle})^2\}$ due to the particle statistics by subtracting counting statistics $\{(\Delta I_{count})^2\}$ from the resulting statistical variance $(\Delta I_{obs})^2$.

In the crystallite size analysis method according to a third aspect, it is further possible to (1) calculate an average intensity (I) from the measured plurality of diffraction beam intensities $\{Ij\}$ (2) calculate the effective number $(n_{eff})$ of diffracting crystallites from the average intensity (I) and the variance $\{(\Delta I_{particle})^2\}$ brought about by the particle statistics, and (3) calculate the effective diameter $(D_{eff})$ of crystallites included in the sample from the effective number $(n_{eff})$ of diffracting crystallites and a known multiplicity of reflection $(m_{eff})$.

The crystallite size analysis apparatus according to the present invention is (1) an apparatus for sampling intensity data of a diffraction beam exiting a powder sample when the sample is irradiated with an x-ray beam, and determining, based on the diffraction beam intensity data, the size of crystallites included in the sample, the apparatus comprising (2) a flat-plate specimen spinner for supporting the sample, (3) an incidence-side optical system for restricting, by using a divergence slit, the width of an x-ray beam emitted by an x-ray source, and irradiating the sample at an incidence angle θ; (4) a receiving-side optical system for allowing the diffraction beam exiting the sample to pass through a scattering slit and a light-receiving slit while restricting the beam width by the slits, receiving the diffraction beam that has passed through the light-receiving slit by an x-ray detector placed at the position of a diffraction angle 2θ, and generating diffraction beam intensity data {Ij} by the x-ray detector, and (5) a controller for controlling the operation of the flat-plate specimen spinner, the incidence-side optical system, and the receiving-side optical system, wherein (6) the controller performs the steps of (i) fixing the x-ray incidence angle θ and diffraction angle 2θ at corresponding intrinsic values on the sample, (ii) rotating the sample within a plane at a designated step angle by the flat-plate specimen spinner, (iii) measuring the diffraction beam intensity by the x-ray detector at the position of each step along the rotation within a plane, (iv) performing an arithmetic operation for calculating the variance $((\Delta I_{particle})^2)$ brought about by particle statistics from the calculated plurality of diffraction beam intensities {Ij}, and (v) performing an arithmetic operation for calculating, based on the variance $\{(\Delta I_{particle})^2\}$ brought about by the particle statistics, the size of the crystallites included in the sample.

EFFECT OF THE INVENTION

The crystallite size analysis method and crystallite size analysis apparatus according to the present invention are designed to calculate, based on the variance $\{(\Delta I_{particle})^2\}$ brought about by particle statistics, the size of crystallites included in a sample, making it possible to evaluate the size of crystallites measuring several micrometers and greater, which could not be measured in the past by conventional analysis methods based on x-ray diffraction line-broadening analysis, by using commonly employed laboratory x-ray diffractometer.

(Premises of the Invention)

It is known that the statistical uncertainty in measured X-ray diffraction intensity data mainly originates from (i) counting statistics and (ii) particle statistics. As used herein, the term "statistics" refers to a technique for studying the distribution of individual elements in a group and quantitatively elucidating the trends, properties, and other characteristics of the group in a unified manner. The term "particle statistics" refers to the statistical variation of a measured intensity brought about by the limited number of crystallites that satisfy certain diffraction conditions. The term "counting statistics" refers to the statistical variation of a measured intensity brought about by fluctuations in the time interval with which x-ray photons exit the x-ray source, and fluctuations in the output provided in a specific direction.

The errors caused by counting statistics can simply be approximated by the square root of the measured number of counts, when the count rate is sufficiently lower than the reciprocal of the response time of the detection system. The inventors recently proposed a practical method to evaluate the statistical errors affected by finite response time of x-ray detection systems (Ida, 2008).

In contrast to the counting statistics, which is a general issue in various fields using nuclear counting, photon counting and neural counting (Teich, 1985), particle statistics is a peculiar problem to the powder diffractometry.

In the pioneering work on this subject by Alexander et al. (1948), theoretical framework about the particle statistics has almost been established. The relative deviation of the diffraction intensity caused by the restricted number of diffracting crystallites is simply given by $$\frac{\Delta I_{particle}}{\langle I \rangle} = \frac{1}{\sqrt{n_{eff}}}, \quad (1)$$

where $n_{eff}$ is the effective number of the crystallites that satisfy the diffraction condition. The effective number $n_{eff}$ is connected with the total number of irradiated crystallites N and the probability p that each crystallite satisfies the diffraction condition, that is $n_{eff}=Np$, when p is much less than unity.

The total irradiated number of crystallites N is given by $$N = \frac{fV}{v_{eff}}, \quad (2)$$

where f is the filling factor of powder sample, and V is the irradiated volume, which is given by $$V = A\mu^{-1} \quad (3)$$

for the cross section of the x-ray beam A, and the linear absorption coefficient of the specimen μ, when the diffraction intensity data are measured using a divergence slit with fixed open angle in symmetric reflection mode.

The effective particle volume $V_{eff}$ in eq. (2) is defined by the ratio of the mean squared volume to the mean volume of crystallites as $$v_{eff} = \frac{\langle v^2 \rangle}{\langle v \rangle}, \quad (4)$$

when the crystallite size distribution is taken into account (Alexander et al., 1948).

Since the linear absorption coefficient μ of powder with filling factor f is given by $\mu=f\mu_0$ for the bulk linear absorption coefficient $\mu_0$, the total irradiated number N is independent of the filling factor, and eq. (2) can be reduced to $$N = \frac{A}{\mu_0 v_{eff}}. \quad (5)$$

The probability P for randomly oriented crystallites in stationary specimens can be approximated by $$P = \frac{m_{eff}\Delta\omega\Delta\chi}{4\pi}, \quad (6)$$

where $m_{eff}$ is the effective multiplicity of reflection, and $\Delta\omega$ and $\Delta\chi$ are the tolerance angles for the normal orientation of the diffraction plane to deviate along equatorial and axial directions, respectively (de Wolff, 1958).

When the effect of rotating specimens is simplified as the expansion of the tolerance area from that of a rectangle $\Delta\omega\Delta\chi$ to a circle $\pi(\Delta\chi)^2/4$, the probability p for crystallites in rotating specimens will be given by $$P = \frac{m_{eff}(\Delta\chi)^2}{16}. \tag{7}$$

The effective multiplicity $m_{eff}$ is defined for an overlapped reflection with component multiplicity $m_j$ and intensity by the following equation (Alexander et al., 1948):

$$m_{eff} = (\Sigma_j m_j I_j)^2/(\Sigma_j m_j I_j^2). \tag{8}$$

The tolerance angles $\Delta\omega$ and $\Delta\chi$ are given by $$\Delta\omega = \frac{w}{R}, \tag{9}$$

$$\Delta\chi = \frac{h}{2R\sin\theta}, \tag{10}$$

where R is the goniometer radius, $\theta$ the Bragg angle, and W and h are the effective width and length of the line-focus of the x-ray source (de Wolff, 1958).

Although the above formulae have been originally intended to describe the statistical properties of the integrated intensity of a diffraction peak (Alexander et al., 1948), they can also be applied to peak intensity, only by modifying the interpretation of the effective width w (de Wolff, 1958). The effective width w for peak intensity is predominantly determined by the geometry of the x-ray source, but it may also be affected by the spectroscopic width of the source x-ray and the width of receiving slit under restriction of diffraction condition. The effective length h is considered to be determined by the open angle $\Phi_A$ of Soller slits, which are commonly adopted in modern Bragg-Brentano diffractometers, as $h = R\Phi_A$ (Smith, 2001).

In a typical case of R=185 mm, W=0.1 mm and $\Phi_A$=5.0°, the probabilities for crystallites in stationary and rotating specimens to satisfy the diffraction condition at a fixed rocking angle are estimated at $p=6.0\times10^{-5}$ and $1.5\times10^{-2}$ for the 111-reflection of Si with multiplicity of m=8 at the diffraction angle $2\theta=28.4°$, and the relative errors caused by particle statistics for 5 μm crystallites in irradiated volume of V=3 mm³ will be about $\Delta I_{particle}/\langle I \rangle$=1.9% and 0.12%, respectively.

It should be emphasized that the improved accuracy by rotating a specimen is mainly caused by the geometry of the diffractometer, where tolerance angle for the normal orientation of the diffraction plane along the axial direction, $\Delta\chi=\Phi_A/2\sin\theta$, is much more generous than that along the equatorial direction, $\Delta\omega=W/R$.

Since the aspect ratio $\Delta\chi/\Delta\omega$ is greater than 100 for lower-angle diffraction peaks, it is expected that slight rotation of the specimen by about 1° has a similar effect to refilling crystalline powder to the sample holder. It is suggested that quantitative analysis about particle statistics can be achieved by simply recording the variation of diffraction intensities on rotation of the specimen.

In this study, we have conducted step-scan diffraction intensity measurements of Si and quartz crystalline powder samples about rotation of specimen at fixed diffraction angles, and examined the validity of the application of the theory proposed by Alexander et al. (1948) to intensity data collected at a fixed rocking angle. It will be shown that quantitative evaluation of crystallite size larger than 1 μm is enabled by applying the method. Other possible applications of the method are also discussed.

DETAILED EXAMINATION OF THE INVENTION

1. Aspect of the Invention

1.1. Samples

Standard Si powder (NIST SRM640c) was used without further grinding or sieving. The median particle size of the Si powder, determined by a laser scattering method, has been reported to be 4.9 μm in the certificate (Freiman & Trahey, 2000).

Three fractions of quartz powder samples were prepared by separating crushed and ground Brazilian quartz crystals by a sedimentation method. The nominal Stokes diameter of the three quartz samples were 3-7, 8-12 and 18-22 μm.

1.2. SEM (Scanning Electron Microscopy) Image Analysis

SEM images of powder samples were taken with a field-emission type scanning electron microscope (JEOL JSM-7000F). Particle images were extracted from SEM images with the aid of a computer software for image analysis (Scion Image). The number of extracted particle images were 1049 for Si, and 1134, 1049 and 1391 for 3-7, 8-12 and 18-22 μm fractions of quartz powder, respectively.

The size of each crystallite was specified as the diameter of the circle with the same area as the particle image.

1.3. Spinner-Scan Measurement

A sample holder with a cylindrical hollow of 30 mmΦ in diameter and 0.6 mm in depth was filled with the powder samples. A home-made specimen spinner attached to a conventional powder diffractometers (Rigaku RAD-2C) with the goniometer radius of R=185 mm was used for step-scan measurements about the rotation angle of specimen. A Cu target sealed tube operated at 40 kV and 30 mA was used as the x-ray source. The take-off angle of the source x-ray beam from the Cu target was about 4°, and the effective width of the x-ray source was estimated at w=0.12 mm from the 2θ-scan intensity profile of the direct beam. The divergence/scattering slit open angles were fixed at $\Phi_{DS/SS}$=1°, and the receiving slit of 0.15 mm width was used. The width of the x-ray beam, measured by locating a fluorescent plate at the specimen position, was $W_{beam}$=10 mm. The cross section of the beam at the specimen position was estimated at $A=W_{beam} R\Phi_{DS/SS}$= 32mm². A curved graphite monochromator attached on the diffracted beam side of the goniometer was adjusted for Cu—Kα wavelength.

Four hundred diffraction intensity data were recorded by rotating the specimen stepwise with the interval of 0.9° over 360°, for each of 11 diffraction peaks at 2θ/θ angles fixed at the peak top positions. The measurement time per step was varied for different reflections, so that at least several hundred counts are collected for each measurement step. The hkl indices of measured reflection, effective multiplicity $m_{eff}$ and the measurement time are listed in Table 1. The effective multiplicity of reflection was estimated based on the results of Rietveld analysis using a software RIETAN developed by Izumi & Ikeda (2000).

TABLE 1

Reflections measured by the spinner scan method.

| Si (NIST SRM640c) | | | α-quartz | | | | |
|---|---|---|---|---|---|---|---|
| hkl | $m_{eff}$ | $FT_0$ (s) | hkl | $m_{eff}$ | $FT_1$ (s) | $FT_2$ (s) | $FT_3$ (s) |
| 111 | 8 | 0.5 | 100 | 6 | 1 | 1 | 1 |
| 220 | 12 | 1 | 101/011 | 9.85 | 0.5 | 0.5 | 0.5 |
| 311 | 24 | 2.5 | 110 | 6 | 2 | 2 | 2 |
| 400 | 6 | 3 | 102/012 | 8.23 | 3 | 2 | 2 |
| 331 | 24 | 6.5 | 111/11$\bar{1}$ | 12 | 5 | 4 | 5 |
| 422 | 24 | 5.5 | 200 | 6 | 3 | 3 | 3 |
| 333/511 | 32 | 12.5 | 201/021 | 10.39 | 5 | 5 | 5 |
| 440 | 12 | 8.5 | 112/11$\bar{2}$ | 12 | 1.5 | 1.5 | 1.5 |
| 531 | 48 | 18 | 202/022 | 9.24 | 5 | 5 | 5 |
| 620 | 24 | 10 | 103/013 | 6.01 | 12 | 9 | 10 |
| 533 | 24 | 19 | 211/121 | 23.72 | 3 | 3 | 3 | hkl is the index of reflection; $m_{eff}$ is the effective multiplicity of reflection; $FT_0$ is measurement time per step for Si, $FT_1$, $FT_2$ and $FT_3$ are for 3-7, 8-12, 18-22 μm quartz samples, respectively.

2. Result and Discussions

2.1. SEM Images

Typical SEM images of a silicon powder (NIST SRM640c) and three types of fractionated α-quartz powder samples are shown in Table 2 and as comparative examples in FIG. 1A and in FIGS. 2A, 2B, and 2C. Extracted particle images of a silicon sample are shown in FIG. 1B.

A cumulative volume distribution of a silicon powder calculated by SEM image analysis is plotted on FIG. 3. Cumulative volume distributions of quartz powders calculated by SEM image analysis are shown in FIGS. 4A, 4B, and 4C.

2.2. Spinner Scan Data of Si Powder

The observed spinner-scan intensity profile of the Si 111 reflection is shown in FIG. 5. Periodic drift in the observed intensity profile, which is likely to be caused by slight misalignment of the sample face, is modeled by Fourier expansion up to the second order. The Fourier coefficients $\{c_k\}$ are calculated by $$c_k = n^{-1} \sum_{j=0}^{n-1} I_j \exp\left(\frac{-2\pi i k j}{n}\right), \quad (14)$$

from the observed intensity data $\{I_j\}$ (j=0 ... n−1), and the profile of periodic drift $\{(I_{drift})_j\}$ is approximated by $$(I_{drift})_j = \sum_{k=-2}^{2} c_k \exp\left(\frac{2\pi i k j}{n}\right). \quad (15)$$

The calculated drift profile is also shown in FIG. 5.

TABLE 2

Results of SEM image analysis of quartz powder.

| Stokes diameter (μm) | 3-7 | 8-12 | 18-22 |
|---|---|---|---|
| ΔD (μm) | 0.2 | 0.4 | 0.8 |
| ρ | −0.0009(0) | −0.0000(0) | −0.0003(0) |
| $D_0$ (μm) | 4.831(6) | 9.239(18) | 21.03(2) |
| ω | 0.2836(11) | 0.2400(12) | 0.1937(11) |
| $(D_{eff})_{raw}$ (μm) | 7.1 | 11.8 | 25.3 |
| $(D_{fit})_{fit}$ (μm) | 7.0 | 12.0 | 27.7 |

ΔD is the assumed error in measured diameter;

ρ is the missing volume fraction under measurable size;

$D_m$ is the median diameter;

ω is the logarithmic standard deviation;

$(D_{eff})_{raw}$ and $(D_{eff})_{fit}$ are the values of effective diameter, evaluated from raw data and optimised fitting parameters, respectively.

The average intensity $\langle I \rangle$ is straightforwardly given by the zero-th order Fourier coefficient $c_0$. The statistical variance of the residuals $(\delta I)_j = I_j - (I_{drift})_j$ is calculated by $$(\Delta I_{obs})^2 = (n-5)^{-1} \sum_{i=0}^{n-1} (\delta I)_j^2, \quad (16)$$

where the degree of freedom is assumed to be decreased by 5, because the second-order Fourier expansion of real data includes 5 independent coefficients determined by the source data. The errors in the evaluated variance, $\Delta[(\Delta I_{obs})^2]$, were calculated by $$\{\Delta[(\Delta I_{obs})^2]\}^2 = \sum_{i=0}^{n-1} \frac{(\delta I)_j^4}{n^2} - \frac{(\Delta I_{obs})^4}{n}. \quad (17)$$

The variance caused by particle statistics, $(\Delta I_{particle})^2$, is calculated from the observed variance $(\Delta I_{obs})^2$ by the equation:

$$(\Delta I_{particle})^2 = (\Delta I_{obs})^2 - (\Delta I_{count})^2, \quad (18)$$

where $(\Delta I_{count})^2$ is the variance caused by the counting statistics, which is approximated by $(\Delta I_{count})^2 \sim \langle I \rangle$.

Then, the effective number of diffracting crystallites $n_{eff}$ is calculated by $$n_{eff} = \frac{\langle I \rangle^2}{(\Delta I_{particle})^2}, \quad (19)$$

for each reflection.

The values of observed average intensity $\langle I \rangle$, statistical variance $(\Delta I_{obs})^2$, statistical variance assigned to particle statistics $(\Delta I_{particle})^2$, and the effective number of diffracting crystallites $n_{eff} = \langle I \rangle^2 / (\Delta I_{obs})^2$, evaluated for the spinner-scan diffraction intensity data of Si powder (NIST SRM640c) are listed in Table 3.

TABLE 3

Results of spinner scan measurements for Si powder (NIST SRM640c).

| hkl | 2θ (°) | <I> | $(\Delta I_{obs})^2$ | $(\Delta I_{particle})^2$ | $n_{eff}$ | $D'_{eff}$ (μm) | $D_{eff}$ (μm) |
|---|---|---|---|---|---|---|---|
| 111 | 28.59 | 2304 (3) | 3440 (260) | 1140 (260) | 4670 (1100) | 4.1 (3) | 5.0 (4) |
| 220 | 47.44 | 2579 (3) | 4890 (340) | 2310 (340) | 2900 (440) | 4.6 (2) | 5.2 (3) |
| 311 | 56.26 | 3266 (4) | 7140 (470) | 3880 (470) | 2750 (340) | 5.6 (2) | 6.1 (3) |
| 400 | 69.24 | 1211 (3) | 2720 (180) | 1510 (180) | 970 (120) | 4.7 (2) | 5.0 (2) |
| 331 | 76.48 | 4157 (5) | 9680 (690) | 5520 (690) | 3130 (400) | 4.9 (2) | 5.2 (2) |
| 422 | 88.12 | 4532 (5) | 10770 (760) | 6240 (760) | 3290 (410) | 4.7 (2) | 5.0 (2) |
| 333/511 | 95.05 | 5028 (6) | 12310 (840) | 7290 (840) | 3470 (410) | 4.9 (2) | 5.4 (2) |
| 440 | 106.79 | 2344 (4) | 5930 (400) | 3590 (400) | 1530 (180) | 4.5 (2) | 5.2 (2) |
| 531 | 114.16 | 9705 (8) | 25800 (2000) | 16100 (2000) | 5860 (740) | 4.6 (2) | 5.4 (2) |
| 620 | 127.60 | 5385 (6) | 13510 (960) | 8100 (960) | 3570 (430) | 4.2 (2) | 5.4 (2) |
| 533 | 136.92 | 6821 (6) | 16200 (1100) | 9400 (1100) | 4950 (600) | 3.7 (2) | 5.2 (2) |

<I> is the average intensity, $(\Delta I_{obs})^2$ is the observed statistical variance, $(\Delta I_{particle})^2$ is the statistical variance assigned to particle statistics, $n_{eff}$ is the effective number of diffracting crystallites, $D'_{eff}$ is the effective diameter calculated from assumed values of geometrical parameters of the diffractometer, and $D_{eff}$ is the calibrated value of effective diameter.

FIG. 6 shows the values of $n_{eff} \sin \theta$ calculated from the spinner-scan data and also the known multiplicity $m_{eff}$ for all the measured reflections of Si powder. It is clearly shown that the variation of the experimental values of $n_{eff} \sin \theta$ is very similar to that of $m_{eff}$. The observed similarity confirms that the particle statistics has certainly been evaluated by the spinner-scan measurement, because no origins for statistical variation except the particle statistics are likely to cause such behaviour as is proportional to the multiplicity of reflection.

The effective diameter of crystallites $D'_{eff}$ is firstly calculated by $$D'_{eff} = \left[ \frac{3 m_{eff} A w \Phi_A}{4\pi^2 n_{eff} \mu_0 R \sin\theta} \right]^{1/3}, \quad (20)$$

according to the formula for stationary specimens given in eq. (6). The values of $D'_{eff}$ for each reflection peak of Si, calculated by assuming $\mu_0 = 142.6$ cm$^{-1}$ and the instrumental parameters: A=32 mm$^2$, w=0.12 mm, $\Phi_A$=5°, and R=185 mm, are also listed in Table 3.

FIG. 7A plots the values of $D'_{eff}$ evaluated for all the measured reflection peaks of Si versus the diffraction angle 2θ. It should be noted that relative error for particle diameter is suppressed by the factor of ⅓ from that of particle volume directly evaluated by spinner-scan measurement. The weighted average of $D'_{eff}$ is nominally estimated at $\overline{D'_{eff}}$=4.52(6) μm, while the corresponding value estimated by the SEM image analysis is $(D_{eff})_{Si}$=5.6 μm.

At this moment, it is difficult to derive an a priori formula for the systematic behaviour of the evaluated effective diameter $D'_{eff}$ depending on the diffraction angle. However, such dependence is likely to be caused by the combination of neglected spectroscopic distribution of the source x-ray, finite receiving slit width, and instrumental aberrations, as has been suggested by de Wolff (1958). When the systematic deviation is assumed to be caused dominantly by the instrumental effect, it is expected that a common calibration curve can be applied to the intensity data from different samples, when they are measured with the same condition.

Taking the uncertainties of the instrumental parameters of the diffractometers on evaluation of $D'_{eff}$ and the above systematic deviation into account, the formula for evaluating the effective diameter $D_{eff}$ should be modified by using the following equation, $$D_{eff} = \frac{D'_{eff}(D_{eff})_{Si}}{(D'_{eff})_{fit}}, \quad (21)$$

where $(D_{eff})_{Si}$=5.6 μm is the value determined by the SEM image analysis, and $(D'_{eff})_{fit}$ is the correction that should be applied to the observed values of $D'_{eff}$.

In this study, the systematic behaviour of $D'_{eff}$ for the Si data is modeled by the following formula depending on the diffraction angle 2θ:

$$(D'_{eff})_{fit} = (D_{eff})_{Si} \left( \frac{t_0}{\tan\theta} + t_1 + t_2 \tan\theta \right)^{-1/3}, \quad (22)$$

because it is expected that the effect of spectroscopic broadening is proportional to tan θ, and the dependence proportional to 1/tan θ is dominant in the effects of instrumental aberrations (Ida & Toraya, 2002). The optimized values of the fitting parameters are estimated at $t_0$=0.62(19), $t_1$=−0.41(45) and $t_2$=1.33(23), by a non-linear least squares fitting method. The fitting curve drawn in FIG. 7A satisfactorily reproduces the observed systematic behaviour.

The formula to evaluate the calibrated value of the effective diameter $D_{eff}$ is then given by $$D_{eff} = \left[ \frac{m_{eff}(138 \, \mu m^2)(0.62/\tan\theta - 0.41 + 1.33 \tan\theta)}{\mu_0 n_{eff} \sin\theta} \right]^{1/3}. \quad (23)$$

The values of the effective diameter $D_{eff}$ calculated by eq. (23) are listed in the last column of Table 3 and also shown in FIG. 7B. Coincidence of the calibrated values $D_{eff}$ evaluated from different reflections of Si is significantly improved from that of crude estimation $D'_{eff}$.

2.3. Spinner Scan Data of Quartz Powder

The spinner-scan intensity data of tree fractions of quartz powder have been analysed in the same manner as the Si powder sample, except that the bulk linear absorption coefficient of $\mu_0$=89.81 cm$^{-1}$ and the known effective multiplicity $m_{eff}$ of α-quartz (see Table 1) are used on calculation of $D'_{eff}$, and the calibration curve $(D_{eff})_{Si}/(D'_{eff})_{fit}$ determined by the Si data are used on estimation of $D_{eff}$.

The values of observed average intensity $\langle I \rangle$, statistical variance $(\Delta I_{obs})^2$, statistical variance assigned to particle statistics $(\Delta I_{particle})^2$, the effective number of diffracting crystallites $n_{eff} = \langle I \rangle^2 / (\Delta I_{particle})^2$, and the crude and calibrated effective diameters, $D'_{eff}$ and $D_{eff}$, evaluated for three fractions of quartz powder are listed in Tables 4-6.

The calibrated values of effective diameter $D_{eff}$ for 11 reflections of three quartz powder samples are plotted in FIG. 8A-8C. No significant systematic deviation of $D_{eff}$ is detected, except that the value estimated for the 100-reflection seems to be overestimated, which may be caused by error on extrapolation of the calibration curve.

TABLE 4

Results of spinner scan measurements for nominally 3-7 μm fraction of quartz powder.

| hkl | 2θ (°) | $\langle I \rangle$ | $(\Delta I_{obs})^2$ | $(\Delta I_{particle})^2$ | $n_{eff}$ | $D'_{eff}$ (μm) | $D_{eff}$ (μm) |
|---|---|---|---|---|---|---|---|
| 100 | 20.77 | 904 (2) | 1180 (80) | 280 (80) | 2960 (870) | 5.6 (5) | 8.2 (8) |
| 101/011 | 26.56 | 2032 (3) | 3000 (200) | 990 (200) | 4170 (870) | 5.4 (4) | 7.3 (5) |
| 110 | 36.46 | 636 (1) | 710 (50) | 80 (50) | 5400 (3600) | 3.8 (8) | 4.7 (1.0) |
| 102/012 | 39.38 | 824 (2) | 1020 (70) | 190 (70) | 3500 (1300) | 4.7 (6) | 5.8 (7) |
| 111/11$\bar{1}$ | 40.23 | 752 (2) | 940 (70) | 190 (70) | 3000 (1000) | 5.6 (7) | 6.8 (8) |
| 200 | 42.37 | 661 (2) | 1000 (70) | 340 (70) | 1300 (280) | 5.8 (4) | 6.9 (5) |
| 201/021 | 45.71 | 737 (1) | 840 (60) | 100 (60) | 5400 (3100) | 4.2 (8) | 5.0 (1.0) |
| 112/11$\bar{2}$ | 50.06 | 717 (2) | 1090 (70) | 370 (70) | 1390 (270) | 6.8 (4) | 7.8 (5) |
| 202/022 | 54.79 | 751 (2) | 990 (70) | 240 (70) | 2390 (660) | 5.1 (5) | 5.7 (5) |
| 103/013 | 55.24 | 802 (2) | 1120 (90) | 320 (90) | 2020 (560) | 4.6 (4) | 5.2 (5) |
| 211/121 | 59.87 | 993 (2) | 1130 (80) | 130 (80) | 7300 (4300) | 4.6 (9) | 5.2 (1.0) |

See Table 3 for definitions.

TABLE 5

Results of spinner scan measurements for nominally 8-12 μm fraction of quartz powder.

| hkl | 2θ (°) | $\langle I \rangle$ | $(\Delta I_{obs})^2$ | $(\Delta I_{particle})^2$ | $n_{eff}$ | $D'_{eff}$ (μm) | $D_{eff}$ (μm) |
|---|---|---|---|---|---|---|---|
| 100 | 20.79 | 825 (5) | 2200 (150) | 1250 (150) | 750 (90) | 8.8 (3) | 12.9 (5) |
| 101/011 | 26.56 | 1641 (8) | 6840 (490) | 4760 (490) | 920 (100) | 9.0 (3) | 12.2 (4) |
| 110 | 36.46 | 550 (4) | 1730 (150) | 1070 (150) | 410 (60) | 9.0 (4) | 11.1 (5) |
| 102/012 | 39.40 | 795 (7) | 1440 (110) | 850 (110) | 410 (50) | 9.7 (4) | 11.8 (5) |
| 111/11$\bar{1}$ | 40.21 | 739 (4) | 1380 (110) | 740 (110) | 560 (80) | 9.9 (5) | 11.9 (6) |
| 200 | 42.37 | 560 (4) | 2190 (150) | 1520 (150) | 290 (30) | 9.5 (3) | 11.4 (4) |
| 201/021 | 45.71 | 673 (4) | 2290 (170) | 1540 (170) | 370 (40) | 10.3 (4) | 12.1 (5) |
| 112/11$\bar{2}$ | 50.06 | 636 (5) | 2180 (150) | 1450 (150) | 360 (40) | 10.6 (4) | 12.2 (4) |
| 202/022 | 54.79 | 663 (6) | 2550 (180) | 1780 (180) | 330 (30) | 9.7 (3) | 11.1 (4) |
| 103/013 | 55.25 | 629 (6) | 2360 (190) | 1740 (190) | 220 (20) | 9.7 (3) | 11.0 (4) |
| 211/121 | 59.88 | 978 (5) | 2390 (190) | 1390 (190) | 720 (100) | 10.0 (5) | 11.3 (5) |

See Table 3 for definitions.

TABLE 6

Results of spinner scan measurements for nominally 18-22 μm fraction of quartz powder.

| hkl | 2θ (°) | $\langle I \rangle$ | $(\Delta I_{obs})^2$ | $(\Delta I_{particle})^2$ | $n_{eff}$ | $D'_{eff}$ (μm) | $D_{eff}$ (μm) |
|---|---|---|---|---|---|---|---|
| 100 | 20.80 | 968 (2) | 8260 (600) | 7430 (600) | 91 (7) | 17.8 (5) | 26.2 (7) |
| 101/011 | 26.57 | 2086 (4) | 27700 (2100) | 26000 (2100) | 103 (9) | 18.6 (5) | 25.3 (7) |
| 110 | 36.47 | 660 (2) | 5330 (440) | 4780 (440) | 63 (6) | 16.7 (6) | 20.7 (6) |
| 102/012 | 39.40 | 591 (2) | 16900 (1500) | 16100 (1500) | 39 (4) | 21.3 (7) | 25.8 (8) |
| 111/11$\bar{1}$ | 40.22 | 643 (2) | 6340 (570) | 5600 (570) | 98 (10) | 17.7 (6) | 21.4 (7) |
| 200 | 42.38 | 668 (2) | 7570 (530) | 7000 (530) | 45 (4) | 17.9 (4) | 21.4 (5) |
| 201/021 | 45.72 | 756 (2) | 7840 (690) | 7170 (690) | 63 (6) | 18.7 (6) | 22.0 (7) |
| 112/11$\bar{2}$ | 50.08 | 727 (2) | 10000 (840) | 9400 (840) | 43 (4) | 21.7 (6) | 25.0 (7) |
| 202/022 | 54.80 | 770 (3) | 12400 (890) | 11740 (890) | 37 (3) | 20.2 (5) | 23.0 (6) |
| 103/013 | 55.26 | 616 (2) | 15100 (1500) | 14500 (1500) | 27 (3) | 19.4 (7) | 21.1 (8) |
| 211/121 | 59.88 | 1001 (2) | 9900 (1700) | 8920 (700) | 107 (8) | 19.0 (5) | 21.4 (6) |

See Table 3 for definitions.

It seems that the errors estimated based on the propagation from the value calculated by eq. (17) are slightly underestimated, but acceptable for the results of 3-7 and 8-12 μm fractions of quartz samples. The uncertainties of $D_{eff}$ evaluated for 18-22 μm quartz sample may be partly caused by the small number of diffracting crystallites $n_{eff}$, ranging only 27-107 for the applied measurement condition. It is suggested that accuracy about size estimation for large crystallites will be improved by expanding the irradiated volume V or by enhancing the probability P, which may be achieved by changing the measurement conditions.

Even though the formula of calibration given by eq. (22) does not have fully concrete theoretical basis, it can be concluded that the dependence on diffraction angle has been successfully removed.

The weighted average values of $\overline{D}_{eff}$ are estimated at 6.5(2), 11.7(2) and 22.8(2) μm for the 3-7, 8-12 and 18-22 μm fractions of quartz powder, while the values estimated by the SEM image analysis were 7.1, 11.8 and 25.3 mm. If there should be any discrepancy, it might be caused by the assumptions on the SEM image analysis rather than the analysis of the spinner-scan data. NIST SRM640c Si powder might not be an ideal material as the standard for evaluation of particle statistics, because of irregular shape and broad size distribution as can be seen in the SEM image (FIG. 1). It is expected that more reliable analysis can be achieved, if standard crystalline powder with more regular shape and narrow size distribution is available.

The method will also be applicable to parallel beam geometry using synchrotron or multi-layer mirror optics, if the effective focal size is evaluated by using standard powder. Use of synchrotron x-ray may expand the sensitivity of the method to smaller crystallite size, because smaller focal size is expected for synchrotron x-ray source.

2.4. Possible Applications of Spinner Scan Method

The results of the current study show that the effective number of crystallites $n_{eff}$ that satisfy the diffraction condition can certainly be measured, simply by rotating the specimen step-wise and recording the diffraction peak intensities.

As has been suggested in section 2.2, "spinner scan data of Si powder", information about multiplicity of measured reflection can be experimentally obtained by the method, without any preliminary knowledge of crystal symmetry or atomic arrangements.

The effective multiplicity of reflection is formally calculated $$m_{eff} = n_{eff} \mu_0 D_{eff}^3 f(\theta), \quad (24)$$

$$f(\theta) = \frac{4\pi^2 R \sin\theta}{3Aw\Phi_A} \left[ \frac{(D'_{eff})_{fit}}{(D_{eff})_{Si}} \right]^3, \quad (25)$$

where the calibration curve $f(\theta)$ is determined by the measurement of the standard sample. The formula of $f(\theta)$ applied in this study is simplified as $$f(\theta) = \frac{\sin(\theta)}{(138 \mu m^2)(0.62/\tan\theta - 0.41 + 1.33\tan\theta)}. \quad (26)$$

Note that the effective number of diffracting crystallites is straightforwardly evaluated by the spinner scan measurement as $n_{eff} = \langle I \rangle^2 / (\Delta I_{particle})^2$. The absorption coefficient $\mu_0$ is obtained from the chemical composition and the density. Then, the value of multiplicity of reflection $m_{eff}$ can be calculated by eq. (24), only if the size of crystallites $D_{eff}$ is determined.

The experimental values of $m_{eff}$ calculated for Si and 8-12 μm fractions of quartz powder samples by eqs. (24) and (26), and the values predicted by the known crystal structures are plotted in FIGS. 9a and 9B. The values of effective diameter $D_{eff}$=5.6 and 12 μm determined by SEM image analysis for Si and quartz samples, respectively, are used for the calculation.

Even though the calibration curve has been adjusted for the Si data, the good coincidence between the predicted and observed values of $m_{eff}$ shown in FIG. 9A indicates that relative values of effective multiplicity $m_{eff}$ can be experimentally evaluated by the method without any standard samples and knowledge about particle size.

The values of $m_{eff}$ for the 8-12 μm quartz powder evaluated by the spinner-scan measurement are absolutely coincided with the values predicted by the crystal structure almost within the experimental errors, as can be seen in FIG. 9B. It means that the absolute value of multiplicity of reflection can be evaluated by this method without any knowledge about the crystal structure, when the effective diameter of crystallites is known. Evaluation of relative values of $m_{eff}$ will be much easier, because it does not need the values of $\mu_0$ and $D_{eff}$. It is thus expected that the method will provide valuable information on determination of unknown structure.

The results presented in section 2.3., "Spinner scan data of quartz powder", show that the size of crystallite over several μm, which cannot be evaluated by line broadening analysis, can certainly be evaluated by the spinner-scan method. The values for different diffraction peaks are well coincided for all the samples examined in this study. It means that the evaluation can be completed by a measurement of the strongest diffraction peak, which will take only several minutes, when the random orientation of crystallites can be assumed.

It is also suggested that the preferred orientation of crystallites may also be evaluated by the method, simply measuring different diffraction peaks, because the number of diffracting crystallites $n_{eff}$ for each reflection should be exactly proportional to the probability that the normal direction of the diffraction plane coincides with the direction normal to the face of the specimen, in principle.

Since the analysis of spinner-scan data provides additional information almost independent of that included in one-dimensional powder diffraction data, application of the method can refine any results of analysis based on powder diffraction data. For example, the method can be used to test the validity of structure models on indexing and structure analysis, and to distinguish a strong diffraction peak of impurity from weak diffraction peaks of main phases in multiphase mixtures by different number of diffraction crystallites $n_{eff}$.

Finally, It is noted that the spinner-scan method is not only applicable to powder samples but also polycrystalline materials for practical use, such as sintered ceramics or alloys.

3. Conclusion

The statistical properties of powder x-ray diffraction intensities measured by a step scan about the rotation angle of a specimen spinning attachment have been investigated.

The results show that the statistical variance assigned to particle statistics can be quantitatively evaluated by the method, and estimation of crystallite size over several μm, which was practically impossible by conventional methods based on line-broadening analysis, has been achieved in considerable accuracy.

It is also suggested that the method is useful for various applications based on powder diffractometry, including determination of unknown structure, structure refinement, evaluation of preferred orientation, qualitative and quantitative analysis of multiphase mixture.

BRIEF DESCRIPTION OF THE DRAWINGS

FIG. 9A is a view showing the effective multiplicity of reflection $m_{eff}$ for silicon;

FIG. 9B is a view showing the effective multiplicity of reflection $m_{eff}$ for a quartz sample;

DESCRIPTION OF THE PREFERRED EMBODIMENTS

A crystallite size analysis method and crystallite size analysis apparatus using powder x-ray diffraction according to the present invention are described below based an embodiment. It shall be apparent that the present invention is not limited by this embodiment. Drawings will be referenced in the description that follows, but the constituent elements in these drawings will sometimes be shown in ratios that differ from the actual ratios in order to make it easier to understand characteristic portions.

Figure 1A:
FIG. 1A is a SEM image of a silicon powder as a comparative example.
Figure 1B:
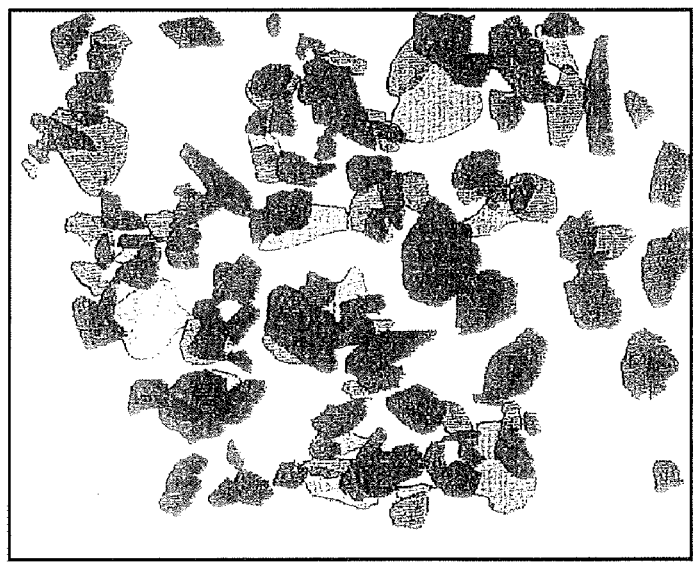
FIG. 1B is a view showing particle profiles extracted from the image of FIG. 1A.
Figure 2A:
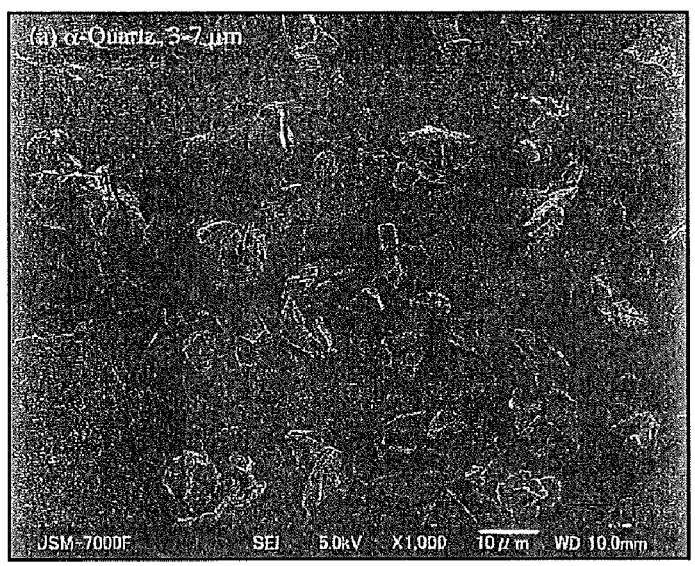
FIG. 2A is a SEM image of a quartz powder fractionated to a size of 3 to 7 μm as a comparative example.
Figure 2B:
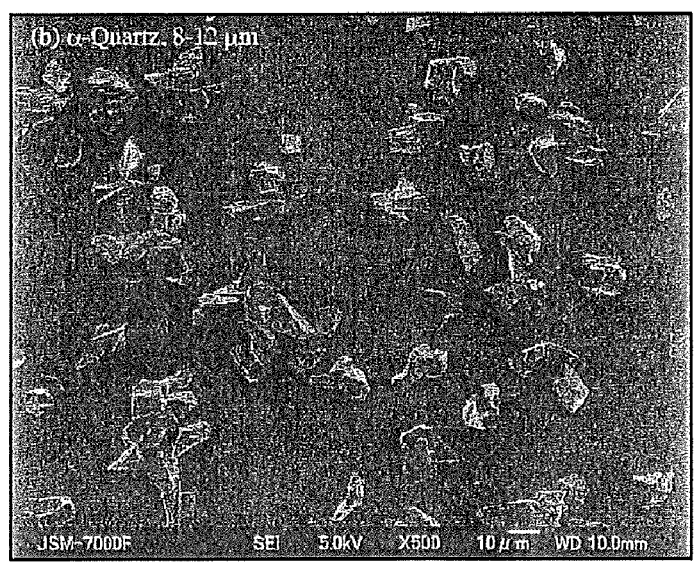
FIG. 2B is a SEM image of a quartz powder fractionated to a size of 8 to 12 μm as a comparative example.
Figure 2C:
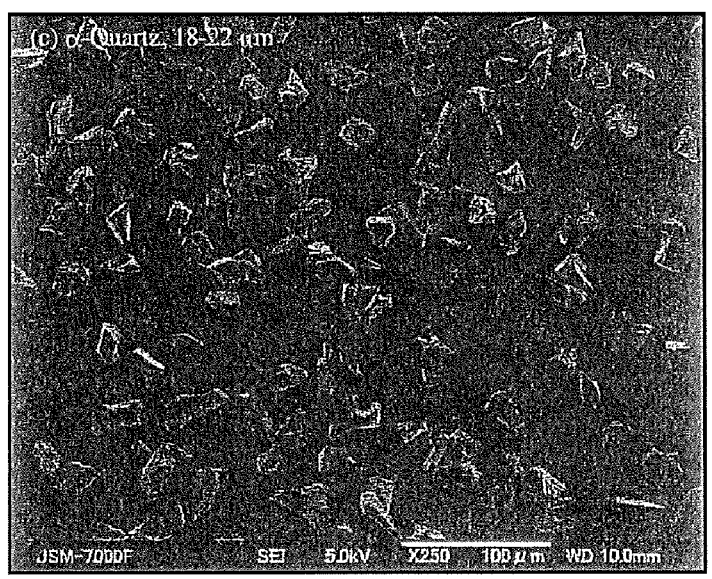
FIG. 2C is a SEM image of a quartz powder fractionated to a size of 18 to 22 μm as a comparative example.
Figure 3:
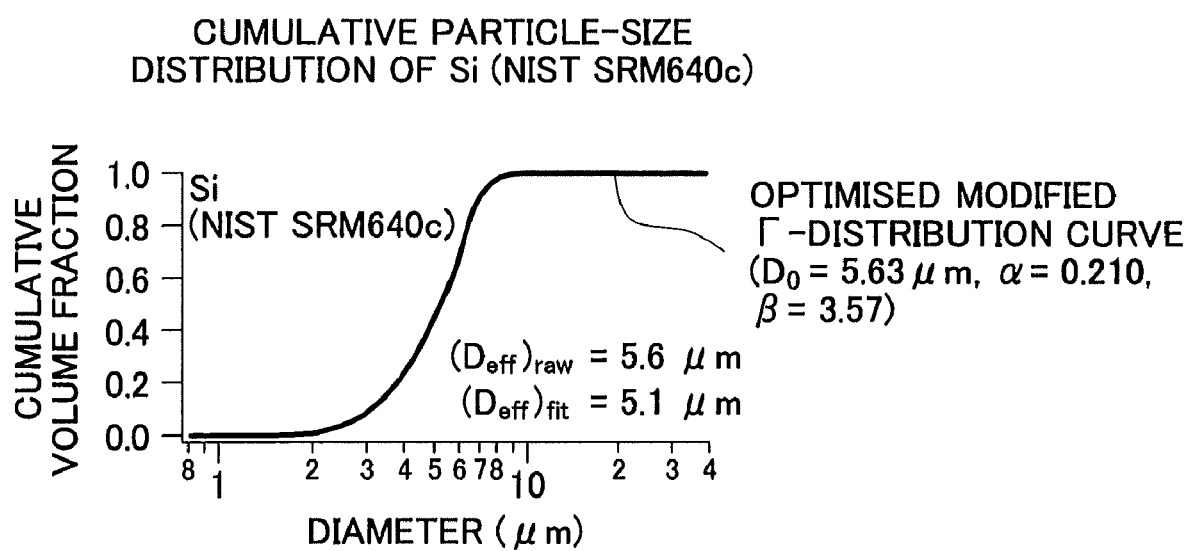
FIG. 3 is a view showing a cumulative volume distribution curve calculated by SEM image analysis as a comparative example.
Figure 4A:
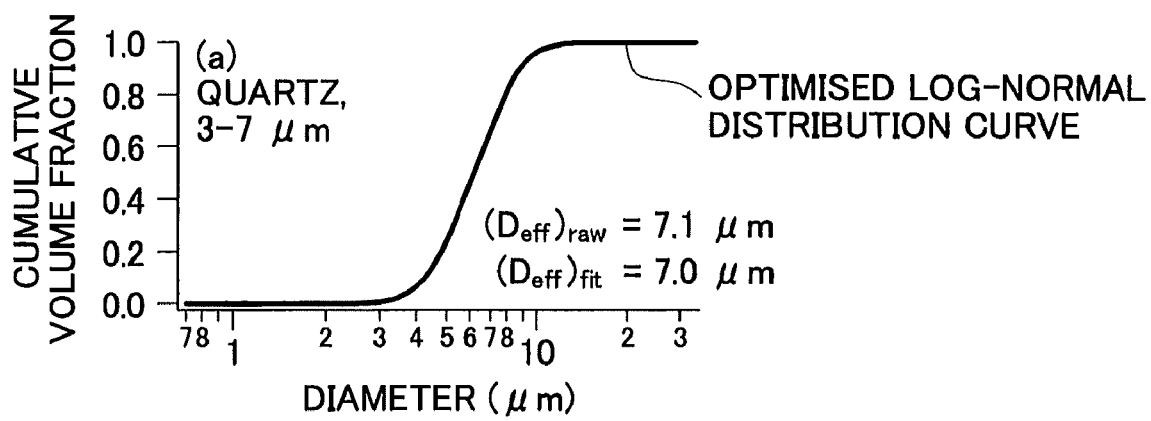
FIG. 4A is a view showing a cumulative volume distribution curve of a quartz sample fractionated to a size of 3 to 7 μm, as calculated by SEM image analysis and presented as a comparative example.
Figure 4B:
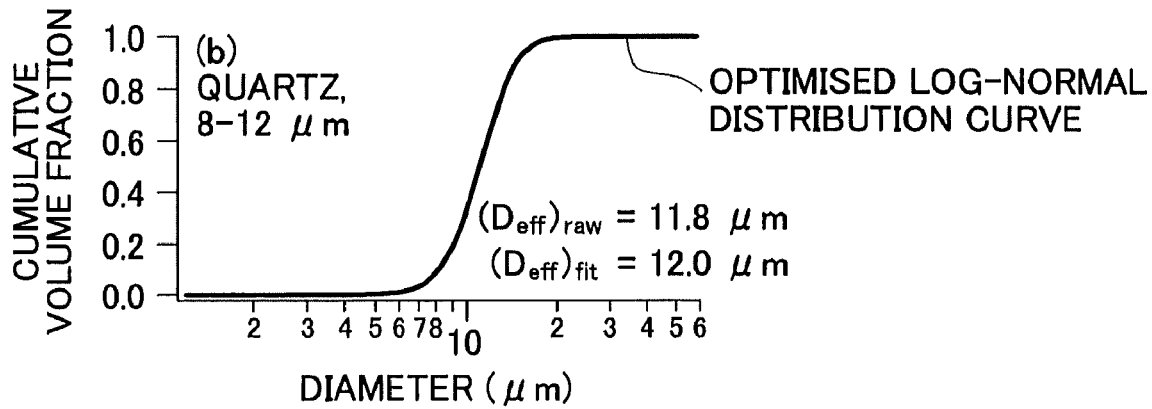
FIG. 4B is a view showing a cumulative volume distribution curve of a quartz sample fractionated to a size of 8 to 12 μm, as calculated by SEM image analysis and presented as a comparative example.
Figure 4C:
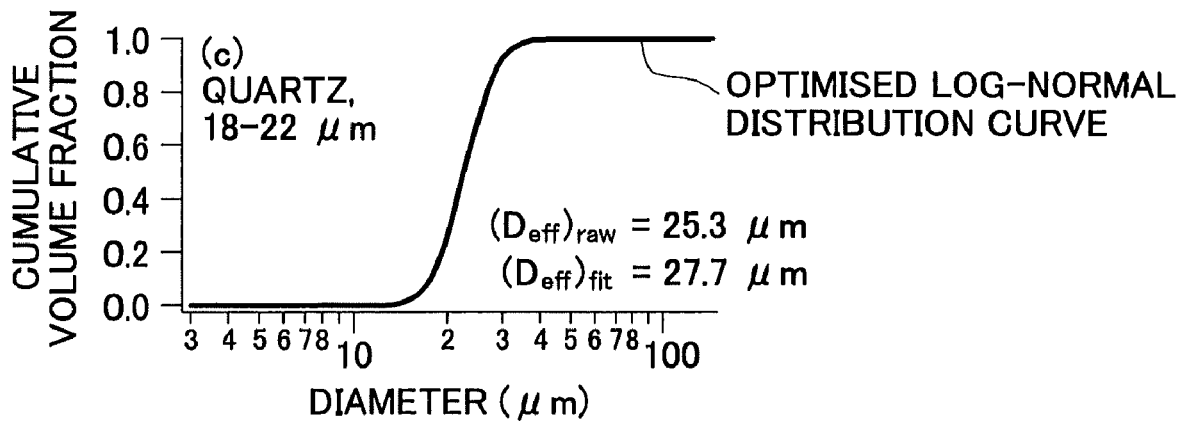
FIG. 4C is a view showing a cumulative volume distribution curve of a quartz sample fractionated to a size of 18 to 22 pin, as calculated by SEM image analysis and presented as a comparative example.
Figure 5:
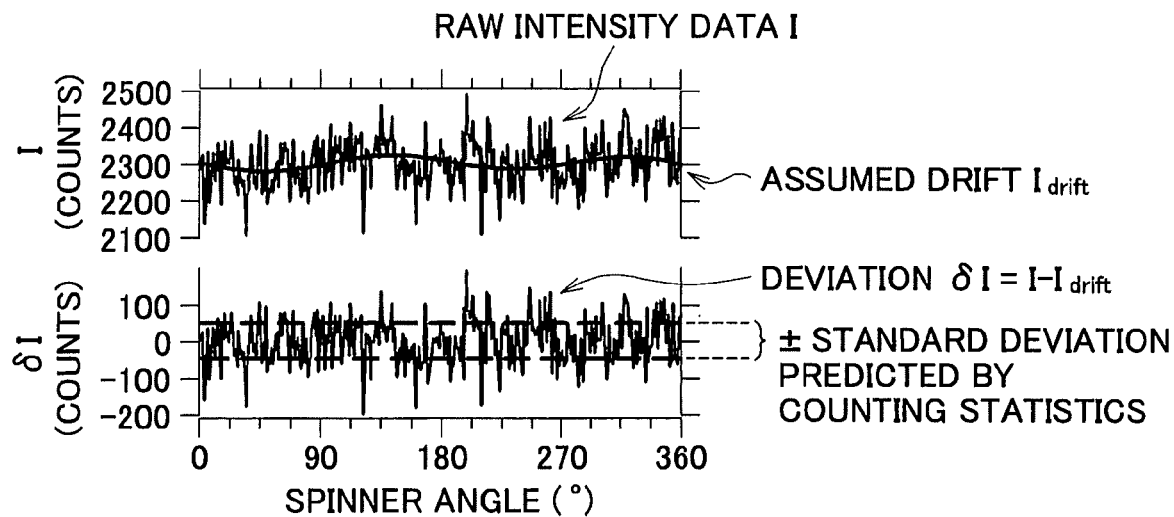
FIG. 5 is a view showing a diffraction intensity profile of silicon related to the present invention.
Figure 6:
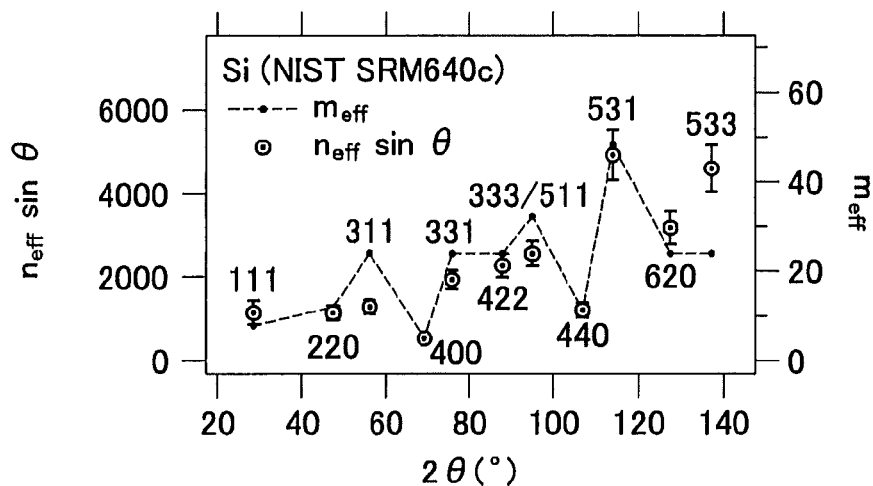
FIG. 6 is a view showing changes in the effective number of crystallites in silicon related to the present invention.
Figure 7A:
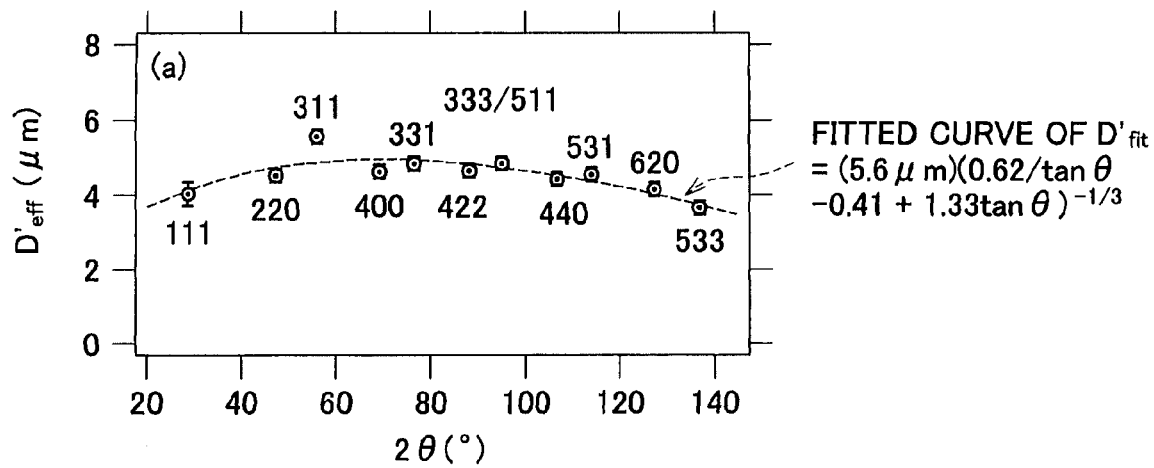
FIG. 7A is a view showing the effective crystal diameter $D_{eff}'$ of silicon related to the present invention, as calculated using assumed instrumental parameters.
Figure 7B:
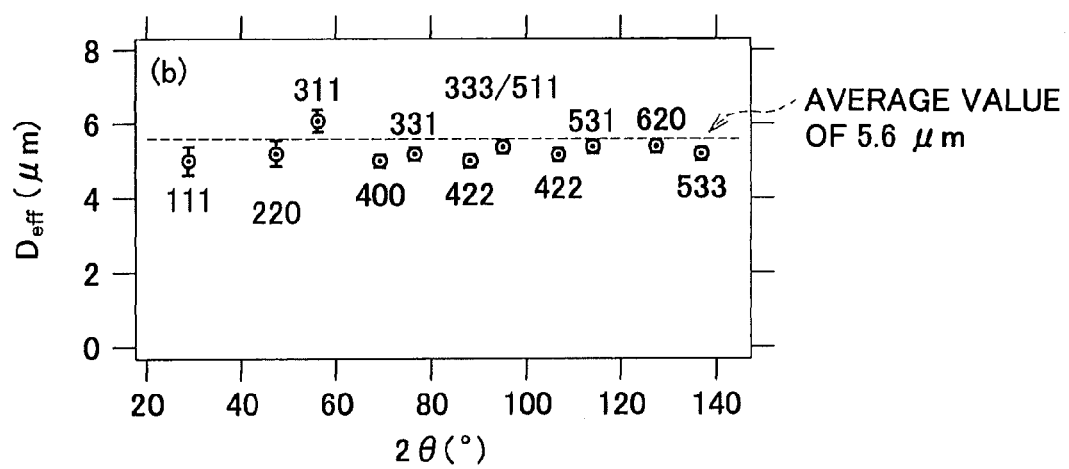
FIG. 7B is a view showing the calibrated effective crystal diameter $D_{eff}$ of silicon.
Figure 8A:
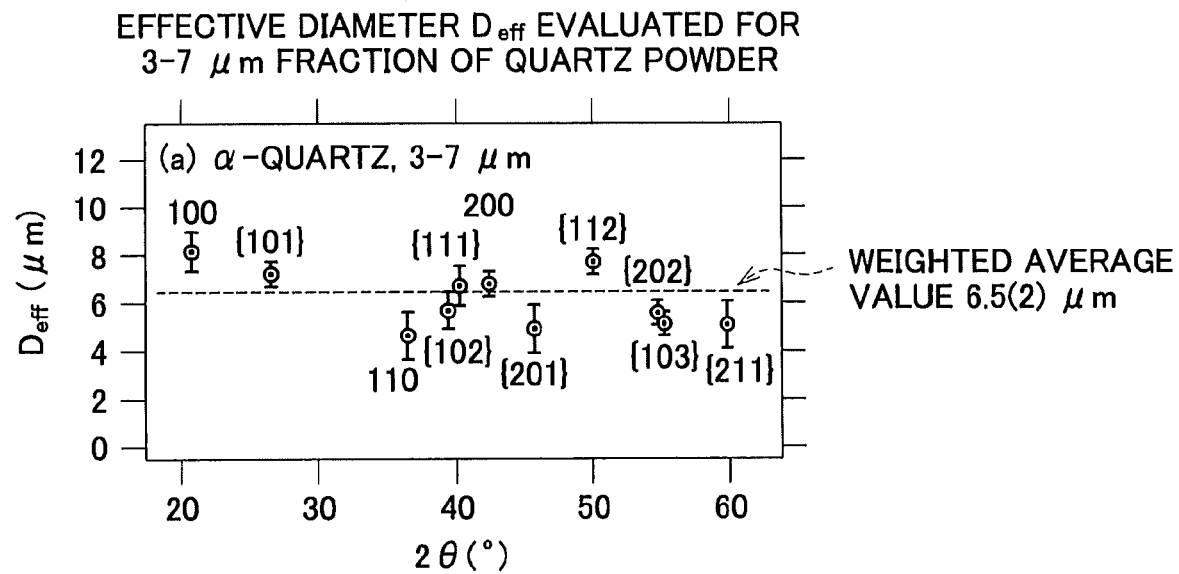
FIG. 8A is a view showing the effective crystal diameter $D_{eff}$ evaluated for the 3-7 μm fraction of quartz powder.
Figure 8B:
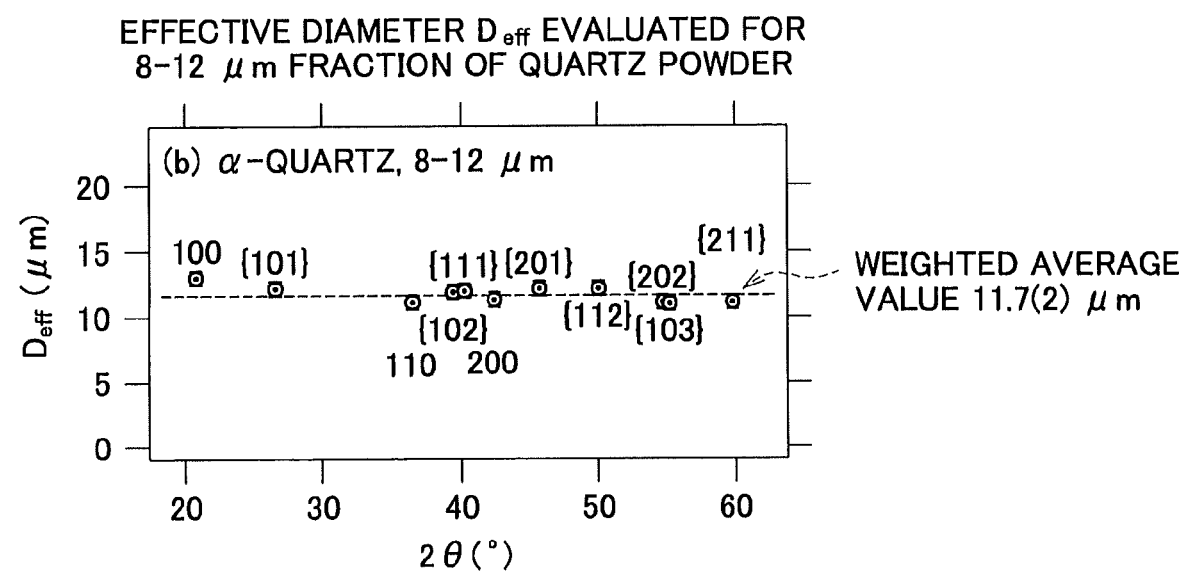
FIG. 8B is a view showing the effective crystal diameter $D_{eff}$ evaluated for the 8-12 μm fraction of quartz powder.
Figure 8C:
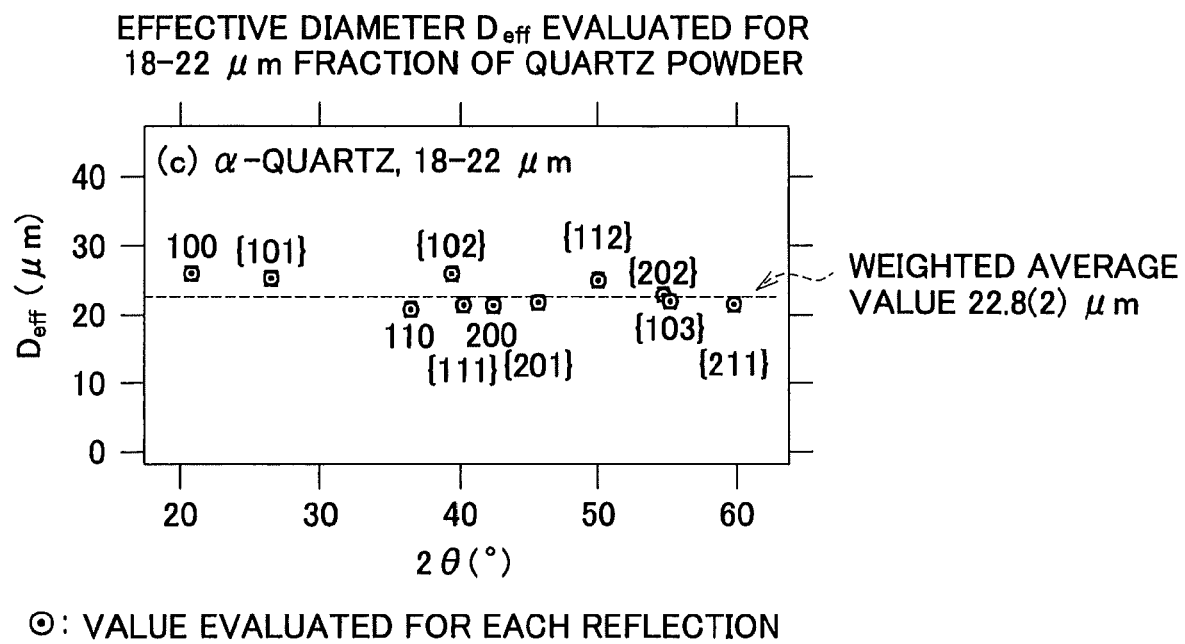
FIG. 8C is a view showing the effective crystal diameter $D_{eff}$ evaluated for the 18-22 μm fraction of quartz powder.
Figure 10:
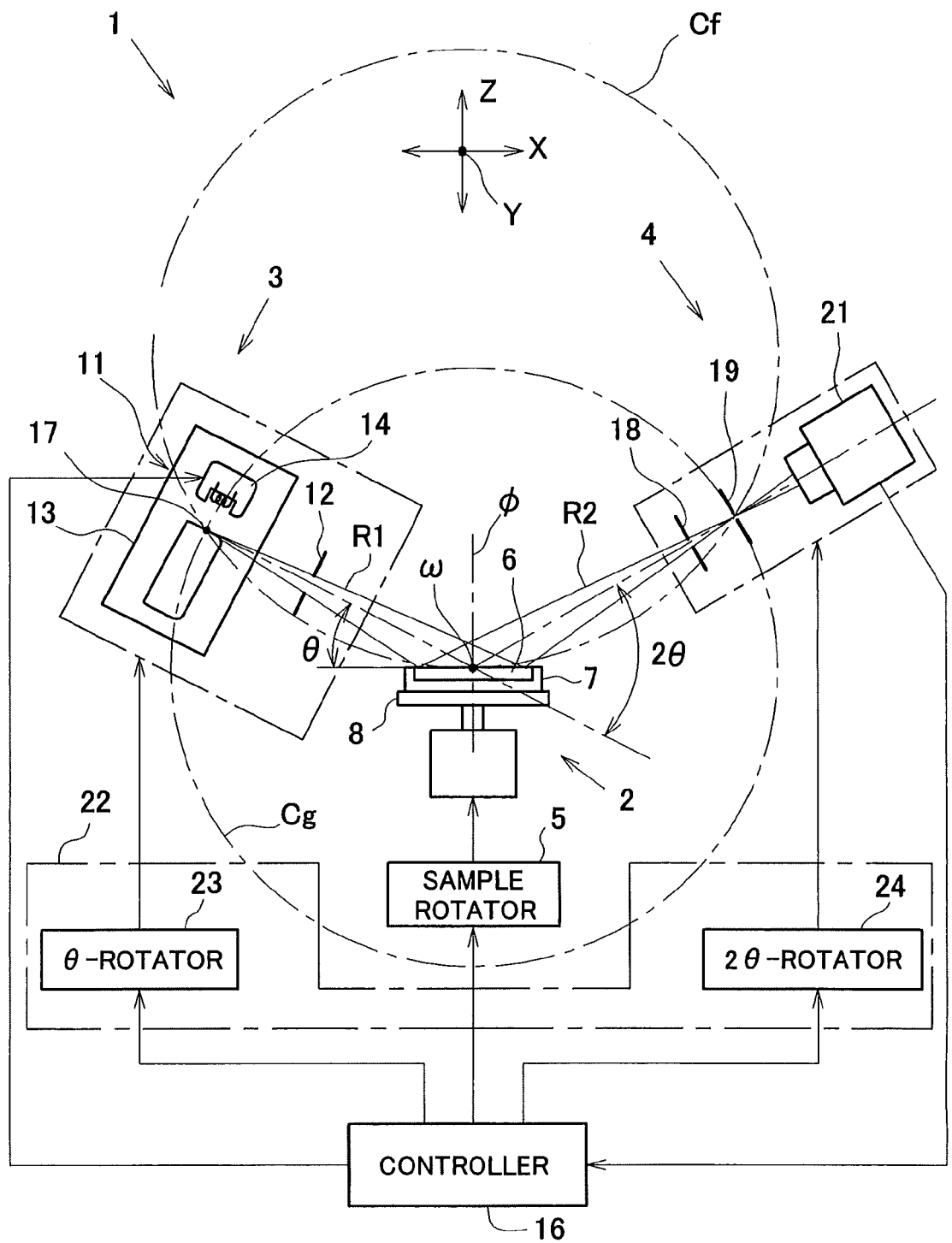
FIG. 10 is a front view of an embodiment of the crystallite size analysis apparatus related to the present invention.
Figure 11:
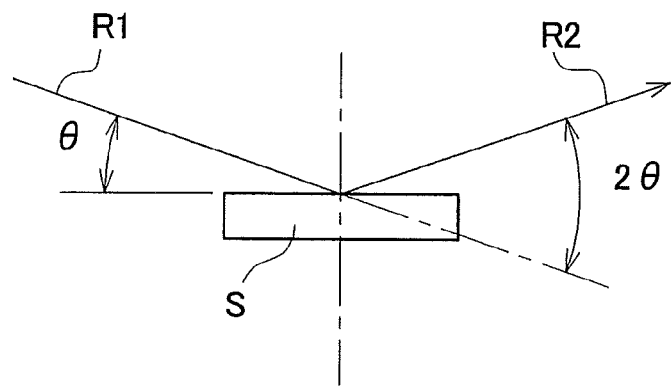
FIG. 11 is a view schematically showing the diffraction of an x-ray beam.
Figure 12:
FIG. 12 is a graph showing an example of a diffraction beam profile.
Figure 13:
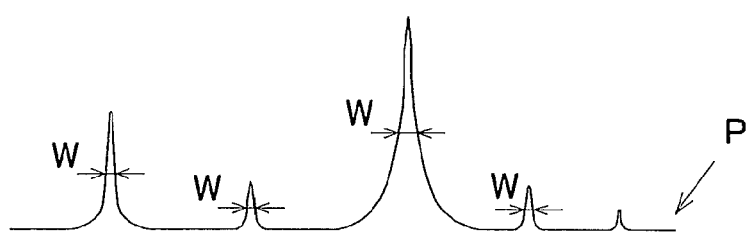
FIG. 13 is a view illustrating x-ray diffraction line-broadening analysis for evaluating the crystallite diameter.

FIG. 10 shows an embodiment of the crystallite size analysis apparatus according to the present invention. The crystallite size analysis apparatus 1 of the embodiment has a flat-plate specimen spinner 2, an incidence-side optical system 3, and a light-receiving optical system 4. In FIG. 10, the Z-axis direction is the vertical direction (i.e., the up-down direction), the X-axis direction is the horizontal direction from left to right, and the Y-axis direction is the front-to-back horizontal direction. Symbol $C_g$ designates a goniometer circle, and symbol $C_f$ designates a focusing circle. The properties of these circular trajectories will be clear from the description that follows.

In this description, the plane containing the X-axis and Y-axis is occasionally referred to as the XY-plane, the plane containing the Y-axis and the Z-axis is occasionally referred to as the YZ-plane, and the plane containing the Z-axis and the X-axis is occasionally referred to as the ZX-plane. Generally, when an x-ray beam incident on a measurement object is scanned and moved across the object, the plane described by the center line of the incident x-ray beam is referred to as the equatorial plane, and the ZX-plane (in the plane of paper in FIG. 10) is the equatorial plane in this embodiment.

The flat-plate specimen spinner 2 has a rotating plate 8, and a specimen holder 7 is mounted on the rotating plate 8. The specimen holder 7 is preferably fixed so as to be prevented from moving from one position to another on the rotating plate 8. The specimen holder 7 is shaped as a disk when viewed, for example, in a plane from the Z-direction, and a cylindrical hollow is formed in the central portion. The hollow is filled with a measurement substance 6. The measurement substance 6 may, for example, be a quartz crystal powder sample or silicon powder (Si) as a standard material.

The flat-plate specimen spinner 2 is provided with a sample rotator 5, and the sample rotator 5 can rotate the rotating plate 8 about an axis φ, that is, within a plane, in accordance with commands from a controller 16. The intra-planar rotation may be accomplished, for example, stepwise, or intermittently, at a designated step angle within a range of 0° to 360° by using a servomotor and a stepping motor. The specimen holder 7 on the rotating plate 8 rotates together with the plate about the axis φ when the plate is rotated within a plane.

As used herein, the point at which the sample 6 supported on the flat-plate specimen spinner 2 intersects with the axis φ, that is, the center point of the sample 6 rotating within a plane, is referred to as the sample center point, and the axis φ is referred to as an intra-planar rotation axis.

The incidence-side optical system 3 has an x-ray generator 11 and a divergence slit 12. The incidence-side optical system 3 may optionally have other x-ray optical elements such as a monochromator and a Soller slit. The x-ray generator 11 has a rotary target 13 whose surface is formed from copper (Cu), and a corresponding filament 14.

The filament 14 is energized in accordance with commands from the controller 16, and is caused to generate heat when energized, and to emit thermal electrons toward a target 13. The thermal electrons collide with the surface of the target 13 at high speed, and an x-ray beam is generated from the target 13 during the collisions. In this embodiment, an x-ray beam that includes CuKα-ray, that is characteristic ray, is emitted, and measurements are primarily performed using the CuKα- ray. The area on the surface of the target 13 where the x-ray beam is generated is an x-ray focal point 17, and the x-ray focal point 17 is referred to as an source x-ray in the present specification. The x-ray can be picked up from the x-ray focal point 17 in two ways: by picking up a point focus and by picking up a line focus, and picking up the line focus is used in the present embodiment.

The x-ray emitted from the x-ray focal point 17 is directed to silicon 6 while the propagation of the beam is restricted by the divergence slit 12. This x-ray beam is the incident x-ray beam R1. The divergence slit 12 primarily restricts the broadening angle of the x-ray beam in the width direction along the ZX-plane (i.e., in the equatorial plane or in the plane of paper in FIG. 10). The broadening angle of the x-ray beam restricted by the divergence slit 12 is commonly referred to as the divergence angle of the divergence slit 12.

The light-receiving optical system 4 has a scattering slit 18, a light-receiving slit 19, and an x-ray detector 21. The light-receiving slit 19 is placed in a position where the diffraction beam R2 generated and converged from the sample 6 is collected, and primarily functions to allow the diffraction beam alone to pass and the unnecessary x-ray beams to be prevented from passing. The width in the direction along the equatorial plane (ZX-plane) of the light-receiving slit 19 is set to a designated value, such as about 0.15 mm to 0.6 mm.

The scattering slit 18 is a slit primarily designed to prevent scattered x-ray beams come from places other than the sample 6, such as x-ray beams scattered by air, from entering the x-ray detector 21. The same divergence angle is usually used for the scattering slit 18 as for the divergence slit 12.

The x-ray detector 21 used in the present embodiment is a zero-dimension x-ray detector. A zero-dimension x-ray detector is an x-ray detector that does not have positional resolution power and may, for example, be composed of a proportional counter, a scintillation counter, or the like. X-ray detectors having linear (i.e., one-dimensional) positional resolution power are one-dimensional x-ray detectors, and x-ray detectors having planar (i.e., two-dimensional) positional resolution are two-dimensional x-ray detectors.

Examples of one-dimensional x-ray detectors include PSPC (position sensitive proportional counters) and CCD (charge coupled devices) linear sensor. Examples of two-dimensional x-ray detectors include sheet-shaped x-ray detectors using accumulation phosphors, and CCD flat sensor. Although a one-dimensional x-ray detector or a two-dimensional x-ray detector can be used in the present invention, a zero-dimension x-ray detector is used in the present embodiment.

The incidence-side optical system 3 and light-receiving optical system 4 are supported by a goniometer (i.e., angle measuring device) 22. In actual practice, the goniometer 22 is a mechanical structure, and is shown in FIG. 10 by a block diagram. The goniometer 22 is a device for varying the angle of each of the incidence-side optical system 3 and light-receiving optical system 4 relative to the flat-plate specimen spinner 2.

The goniometer 22 has a θ-rotator 23 and a 2θ-rotator 24. The θ-rotator 23 is a device for rotatably driving the incidence-side optical system 3 about an axis ω. The 2θ-rotator 24 is a device for rotatably driving the light-receiving optical system 4 about the axis ω. These devices 23, 24 may, for example, be configured so that a servomotor or pulse motor is used as the drive source, and the drive force thereof is transmitted via a power force transmission system such as a worm or a worm wheel.

Pulse motors are used as the drive sources for the rotators 23, 24 in the present embodiment, and pulse signals for controlling the rotational speed and rotational angle of the pulse motors are transmitted to the rotators 23, 24 from the controller 16. The controller 16 can determine both the angles θ and 2θ on the basis of the number of pulses in the pulse signal.

The axis ω is a line that lies in the plane containing the surface of the sample 6, and is orthogonal to the in-plane rotation axis φ. When the incidence-side optical system 3 is rotatably driven by the θ-rotator 23 about the axis ω, variations occur in the angle θ formed by the x-ray beam (i.e., incident x-ray beam) R1 that exits from the x-ray focal point 17 and strikes the sample 6, in relation to the sample 6. The plane described by the center line of the incident x-ray beam R1 during variation of the incidence angle θ is the equatorial plane (ZX-plane). The angle 2θ formed by the line of sight from the x-ray detector 21 to the center position of the sample 6 and the extension of the incident x-ray beam R1 varies when the light-receiving optical system 4 is rotatably driven by the 2θ-rotator 24 about the axis ω. The axis ω will be referred to hereinbelow as the sample axis or the sample center axis.

The operation of the θ-rotator 23 or 2θ-rotator 24 in the goniometer 22 is controlled by the controller 16. Specifically, when the x-ray incidence angle θ varies, the operation is controlled so that the angle 2θ at which the sample 6 is viewed from the x-ray detector 21 is constantly kept at twice the value of the x-ray incidence angle θ. As a result, the light-receiving optical system 4 is driven by the 2θ-rotator 24 and is rotated about the axis ω at the same angular velocity as the incidence-side optical system 3 in the opposite direction from the incidence-side optical system 3 when the incidence-side optical system 3 is driven by the θ-rotator 23 and rotated about the axis ω in the clockwise direction or counterclockwise direction in FIG. 10. The operation is thereby controlled so that the angle 2θ at which the sample 6 is viewed from the x-ray detector 21 is constantly kept at twice the x-ray incidence angle θ.

A configuration is adopted in the present embodiment in which the flat-plate specimen spinner 2 is fixedly arranged so as not to move from position to position, and the incidence-side optical system 3 and the light-receiving optical system 4 are rotatably moved in mutually opposite directions about the axis ω at the same angular velocity θ. However, this arrangement can be replaced with one in which the incidence-side optical system 3 is fixedly arranged, the flat-plate specimen spinner 2 is rotated at an angular velocity θ about the axis ω, and the light-receiving optical system 4 is rotated in the same direction as specimen spinner 2 at the double rotational velocity 2θ.

The goniometer circle $C_g$ is a circular trajectory described by the x-ray focal point 17 in the incidence-side optical system 3 and by the light-receiving slit 19 in the light-receiving optical system 4 when the incidence-side optical system 3 and the light-receiving optical system 4 rotatably move about the sample center axis ω. In addition, the focusing circle $C_f$ is a circular trajectory formed by the three points of the x-ray focal point 17, the sample center point (point of intersection between the axes φ and ω), and the light-receiving slit 19.

The goniometer circle $C_g$ is a circle that always has a constant radius, and the focusing circle $C_f$ is a circle whose radius varies in accordance with variations in the x-ray incidence angle θ and the angle 2θ of the x-ray detector 21 in relation to the incident x-ray beam R1. The radius of the goniometer circle $C_g$ is commonly referred to as the goniometer radius. In the present embodiment, the goniometer radius is set to 185 mm.

The central optical axis of the incident x-ray beam R1 and the central optical axis of the diffraction beam R2 move in a single plane about the sample axis ω when the incidence-side optical system 3 and the light-receiving optical system 4 rotatably move about the sample axis ω. The single plane is the equatorial plane. The sample axis ω is a line orthogonal to the equatorial plane, and the intra-planar rotation axis φ is a line that lies in the equatorial plane. Also, the goniometer circle $C_g$ and the focusing circle $C_f$ are both circular trajectories that lie in the equatorial plane.

The controller 16 is composed of a computer having a CPU (central processing unit), RAM (random access memory), ROM (read only memory), memory, and the like. The analysis program software designed to allow each equipment element to function in order to be able to detect the size of the crystallites, or the crystallite size, is loaded in the memory.

Figure 14:
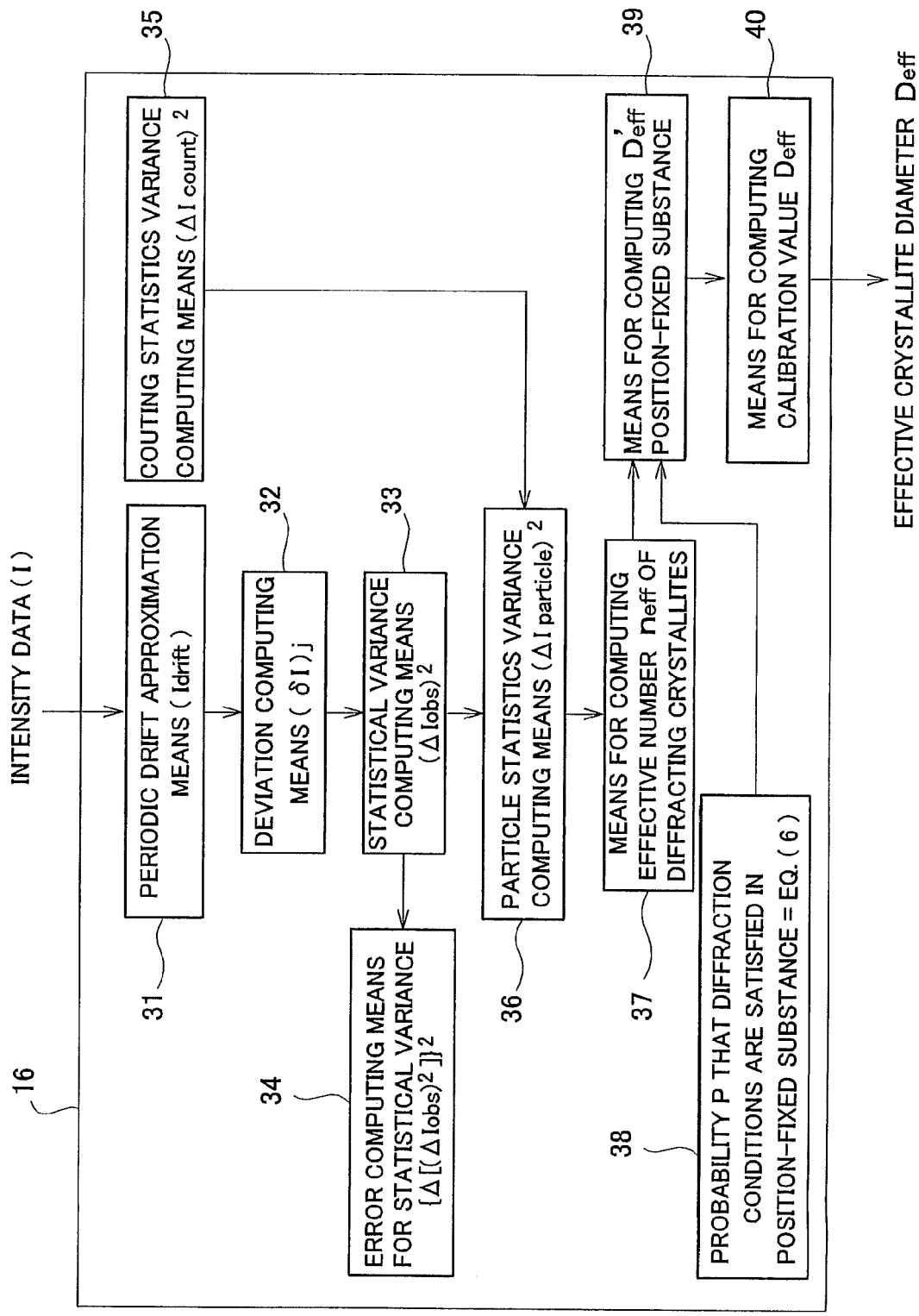
FIG. 14 is a block diagram showing the functions provided by a controller.

The operation of the crystallite size analysis apparatus 1 thus configured will now be described with reference to the functional diagram shown in FIG. 14. In FIG. 14, the series of functions performed when the controller 16 operates in accordance with the analysis program software is shown as a block diagram.

(Measurement of Silicon Powder as Standard Substance)

The specimen holder 7 in FIG. 10 is filled with a measurement substance 6 such as a silicon powder, which is a standard substance. The specimen holder 7 is fixed on the rotating plate 8 of the flat-plate specimen spinner 2. A plurality of x-ray incidence angles θ at which diffraction occurred in the silicon 6, and a plurality of the corresponding angles 2θ of the x-ray detector 21, are selected as reflection positions, and these angles are stored in the designated areas of the memory arranged in the analysis program.

The controller 16 brings the incidence-side optical system 3 and light-receiving optical system 4 into one of the selected plurality of reflection positions (θ, 2θ).

In this state, the flat-plate specimen spinner 2 is operated by the sample rotator 5, and the silicon 6 is rotatably scanned within a plane at a designated step angle about the intra-planar rotation axis φ.

A diffraction beam R2 is generated from the silicon 6 once the diffraction conditions between the sample 6 and the x-ray beam R1 incident on the silicon 6 are satisfied when the silicon scanned and moved within a plane is brought to each of the step positions.

The resulting diffraction beam R2 is received and counted by the x-ray detector 21, the counting result is output as a diffraction beam intensity signal from the x-ray detector 21, and the output signal is transmitted to the controller 16.

The diffraction beam intensity is measured in this manner for the entire plurality of selected reflection positions (θ, 2θ), and the diffraction beam intensity data $\{I_j\}$ (j=0, ..., n−1) at each of the reflection locations is stored in a designated area within the memory of the controller 16.

A periodic drift approximation means 31 shown in FIG. 14 and included in the controller 16 subsequently calculates, based on the transmitted diffraction beam intensity data $\{I_j\}$, the Fourier coefficient $c_K$ according to the following formula:

$$c_k = n^{-1} \sum_{j=0}^{n-1} I_j \exp\left(\frac{-2\pi i k j}{n}\right) \tag{14}$$

and calculates the profile of the periodic drift $\{(I_{drift})_j\}$ according to the following formula:

$$(I_{drift})_j = \sum_{k=-2}^{2} c_k \exp\left(\frac{2\pi i k j}{n}\right) \tag{15}$$

A deviation computing means 32 subsequently subtracts the drift component from the measured intensity to calculate the deviation (δI)j in accordance with the following formula:

$$(\delta I)_j = I_j - (I_{drift})_j$$

Furthermore, a statistical variance computing means 33 calculates the statistical variance $(\Delta I_{obs})^2$ of the deviation (δI) according to the following formula:

$$(\Delta I_{obs})^2 = (n-5)^{-1} \Sigma_{i=0}^{n-1} (\delta I)_j^2 \tag{16}$$

It is thus possible to correctly evaluate the particle diameter by calculating the variance $(\Delta I_{obs})^2$ after taking the periodic drift into account.

The error $\Delta[(\Delta I_{obs})^2]$ in the evaluated variance is subsequently calculated by an error computing means 34 for the statistical variance according to the following formula:

$$\{\Delta[(\Delta I_{obs})^2]\}^2 = \sum_{t=0}^{n-1} \frac{(\delta I)_j^4}{n^2} - \frac{(\Delta I_{obs})^4}{n} \tag{17}$$

Here, the error of the resulting efficient diameter $D_{eff}$ can be ultimately obtained by calculating the error $\Delta[(\Delta I_{obs})^2]$.

A counting statistics variance computing means 35 functionally implemented by the controller 16 calculates the variance $(\Delta I_{count})^2$ brought about by the counting statistics. $(\Delta I_{count})^2$ is usually approximated by $(\Delta I_{count})^2 \sim \langle I \rangle$. The resulting signal is transmitted to a particle statistics variance computing means 36.

The particle statistics variance computing device 36 calculates, based on the output signal of the statistical variance computing means 33 and the output signal of the counting statistics variance computing means 35, the variance $(\Delta I_{particle})^2$ brought about by the particle statistics in accordance with the following formula:

$$(\Delta I_{particle})^2 = (\Delta I_{obs})^2 - (\Delta I_{count})^2 \tag{18}$$

Means 37 for computing the effective number of diffracting crystallites calculates the effective number $n_{eff}$ of diffracting crystallites on the basis of the output signal of the particle statistics variance computing means 36 in accordance with the following formula:

$$n_{eff} = \frac{\langle I \rangle^2}{(\Delta I_{particle})^2} \tag{19}$$

Means 38 for computing the probability that diffraction conditions are satisfied in a position-fixed substance calculates, in accordance with the formula shown below, the prob ability p that randomly oriented crystals in a position-fixed substance will satisfy the diffraction conditions.

$$p = \frac{m_{eff} \Delta\omega \Delta\chi}{4\pi} \quad (6)$$

Means 39 for computing the diameter of particles in a position-fixed substance calculates, in accordance with the formula shown below, the effective diameter $D_{eff}'$ of crystallites in a position-fixed sample on the basis of the output signal of the device 37 for computing the effective number of diffracting crystallites, and the output signal of the device 38 for computing the probability that diffraction conditions are satisfied in a position-fixed substance.

$$D_{eff}' = \left[ \frac{3 m_{eff} A w \Phi_A}{4\pi^2 n_{eff} \mu_0 R \sin\theta} \right]^{1/3} \quad (20)$$

Means 40 for computing the calibration value of particle diameters calculates, in accordance with the formula shown below, the calibrated effective diameter $D_{eff}$ on the basis of $D_{eff}'$, which is the output of the device 39 for computing the diameter of particles in a position-fixed substance.

$$D_{eff} = \left[ \frac{m_{eff}(138 \ \mu m^2)(0.62/\tan\theta - 0.41 + 1.33\tan\theta)}{\mu_0 n_{eff} \sin\theta} \right]^{1/3} \quad (23)$$

$D_{eff}$ is the silicon crystallite diameter calculated using the crystallite size analysis apparatus 1 of the present embodiment. Crystallites of various diameters are commonly present in a silicon powder substance, and the crystallite diameter referred to herein corresponds to a mean crystallite diameter. Silicon is a standard substance, and the actual crystallite diameter is known, for which reason the final calibration coefficient can be calculated based on the calculated $D_{eff}$ and the known crystallite diameter. The calculated $D_{eff}$ and calculated $D_{eff}'$ are stored in a designated area of the memory in the controller 16.

(Measurement of Quarts Powder)

The specimen holder 7 in FIG. 10 was filled with a quartz power sample having an unknown crystallite size. Substantially the same measurements as the silicon measurements described above were carried out and the crystallite diameter $D_{eff}$ was calculated. The measurements had the following differences from those involving silicon.

(1) $D_{eff}'$ was calculated by using the linear absorption coefficient of $\mu_0$ and the effective multiplicity of quartz $m_{eff}$, where $\mu_0 = 89.81 \ cm^{-1}$ was used for the crystals.

(2) The known effective multiplicity of quartz $m_{eff}$ (see Table 1) was used in the $D_{eff}'$ calculations.

(3) A calibration curve $(D_{eff})_{Si}/(D_{eff}')_{fit}$ determined by silicon data was used in the $D_{eff}$ evaluations.

Extremely accurate and objective measurement results were obtained for crystallite diameters because the $D_{eff}$ obtained as a result of measurements and calculations was calibrated based on the results for silicon, which is a standard substance, as in (3) above.

Other Embodiments

In the embodiment shown in FIG. 10, a zero-dimension x-ray detector was used as the x-ray detector 21, and the angle 2θ of the x-ray detector 21 was scanned and moved when the x-ray incidence angle θ was scanned and moved. This arrangement may be replaced with an arrangement in which the x-ray detector is composed of a unidimensional x-ray detector or a two-dimensional x-ray detector having positional resolution power in the 2θ direction, and the scanning movement of the angle 2θ by the x-ray detector is replaced with the positional resolution power of the x-ray detector.

What is claimed is:

1. A crystallite size analysis method using powder x-ray diffraction for sampling intensity data of a diffraction beam generated from a powder sample when the sample is irradiated with an x-ray beam, and determining, based on the diffraction beam intensity data, the size of crystallites included in the sample, said method comprising the steps of:
    supporting the sample on a flat rotary specimen stage;
    restricting, by using a divergence slit, the width of an x-ray beam emitted by an x-ray source, and irradiating the sample at an incidence angle θ;
    allowing the diffraction beam generated from the sample to pass through a scattering slit and a light-receiving slit while restricting the beam width by the slits;
    receiving the diffraction beam that has passed through the light-receiving slit by an x-ray detector placed at the position of a diffraction angle 2θ, and generating diffraction beam intensity data(Ij) (j=0,1, . . . ,n−1) by the x-ray detector;
    fixing the x-ray incidence angle θ and diffraction angle 2θ at corresponding intrinsic values on the sample;
    rotating the sample within a plane at a designated step angle by the flat rotary specimen stage;
    measuring the diffraction beam intensity (Ij) by the x-ray detector at the position of each step along the rotation within a plane and storing each measured diffraction beam intensity (Ij) in a memory;
    calculating, by a controller, a variance $((\Delta I_{particle})^2)$ due to particle statistics from the measured plurality of diffraction beam intensities (Ij) and storing the variance $((\Delta I_{particle})^2)$ in the memory; and
    calculating, by a controller, based on the variance $((\Delta I_{particle})^2)$ due to the particle statistics, the size of the crystallites included in the sample.

2. The crystallite size analysis method according to claim 1, wherein the step of calculating the variance $((\Delta I_{particle})^2)$ due to a particle statistics from the measured plurality of diffraction beam intensities (Ij) comprises:
    calculating, by the controller periodic drift $(I_{drift})$ from the measured plurality of diffraction beam intensities (Ij);
    calculating, by the controller, the statistical variance $((\Delta I_{obs})^2)$ of deviation (δI) which is obtained by subtracting the periodic drift $(I_{drift})$ from the measured plurality of diffraction beam intensities;(Ij); and
    calculating, by the controller, the variance $((\Delta I_{particle})^2)$ due to the particle statistics by subtracting counting statistics $((\Delta I_{count})^2)$ from the resulting statistical variance $((\Delta I_{obs})^2)$.

3. The crystallite size analysis method according to claim 2, wherein the step of calculating the size of the crystallites included in the sample comprises:
    calculating, by a controller, an average intensity (I) from the measured plurality of diffraction beam intensities (Ij);
    calculating, by the controller the effective number $(n_{eff})$ of diffracting crystallites from the average intensity (I) and the variance $((\Delta I_{particle})^2)$ due to the particle statistics; and
    calculating, by the controller, the effective diameter $(D_{eff})$, as the size of crystallites included in the sample from the effective number $(n_{eff})$ of diffracting crystallites and a known multiplicity of reflection $(m_{eff})$.

4. A crystallite size analysis apparatus using powder x-ray diffraction for sampling intensity data of a diffraction beam generated from a powder sample when the sample is irradiated with an x-ray beam, and determining, based on the diffraction beam intensity data, the size of crystallites included in the sample, said apparatus comprising:

a flat rotary specimen stage for supporting the sample;

an incidence-side optical system for restricting, by using a divergence slit, the width of an x-ray beam emitted by an x-ray source, and irradiating the sample at an incidence angle $\theta$;

a receiving-side optical system for allowing the diffraction beam generated from the sample to pass through a scattering slit and a light-receiving slit while restricting the beam width by the slits, receiving the diffraction beam that has passed through the light-receiving slit by an x-ray detector placed at the position of a diffraction angle $2\theta$, and generating diffraction beam intensity data by the x-ray detector; and a controller for controlling the operation of the flat rotary specimen stage, the incidence-side optical system, and the receiving-side optical system wherein:

the controller fixes the x-ray incidence angle $\theta$ and diffraction angle $2\theta$ at corresponding intrinsic values on the sample, rotates the sample within a plane at a designated step angle by the flat rotary specimen stage, measures the diffraction beam intensity with the x-ray detector at the position of each step along the rotation within a plane and stores the diffraction beam intensity in a memory, performs an arithmetic operation for calculating a variance due to particle statistics from the measured plurality of diffraction beam intensities (Ij) and stores the variance $((\Delta I_{particle})^2)$ in the memory, and performs an arithmetic operation for calculating, based on the variance due to the particle statistics, the size of the crystallites included in the sample.

* * * * *